United States Patent
Chandran et al.

(10) Patent No.: US 8,027,888 B2
(45) Date of Patent: Sep. 27, 2011

(54) ONLINE CREDIT CARD PRESCREEN SYSTEMS AND METHODS

(75) Inventors: Rohan K. K. Chandran, Sunnyvale, CA (US); Richard Rodenbusch, Allen, TX (US); Shawn Mendelovich, San Francisco, CA (US)

(73) Assignee: Experian Interactive Innovation Center, LLC, San Mateo, CA (US)

( * ) Notice: Subject to any disclaimer, the term of this patent is extended or adjusted under 35 U.S.C. 154(b) by 315 days.

(21) Appl. No.: 11/537,330

(22) Filed: Sep. 29, 2006

(65) Prior Publication Data

US 2008/0059317 A1 Mar. 6, 2008

Related U.S. Application Data

(60) Provisional application No. 60/824,258, filed on Aug. 31, 2006, provisional application No. 60/824,252, filed on Aug. 31, 2006.

(51) Int. Cl.
G07B 17/00 (2006.01)
G07F 19/00 (2006.01)
G06Q 40/00 (2006.01)

(52) U.S. Cl. .......................... 705/30; 705/35
(58) Field of Classification Search .......... None
See application file for complete search history.

(56) References Cited

U.S. PATENT DOCUMENTS

| | | | |
|---|---|---|---|
| 5,819,234 A | 10/1998 | Slavin et al. | |
| 5,822,410 A | 10/1998 | McCausland et al. | |
| 5,870,721 A | 2/1999 | Norris | |
| 5,878,403 A | 3/1999 | DeFrancesco et al. | |
| 5,907,828 A | 5/1999 | Meyer et al. | |
| 5,924,082 A | 7/1999 | Silverman et al. | |
| 5,930,776 A | 7/1999 | Dykstra et al. | |
| 5,940,812 A | 8/1999 | Tengel et al. | |
| 5,966,699 A | 10/1999 | Zandi | |

(Continued)

FOREIGN PATENT DOCUMENTS

EP 1 028 401 A2 8/2000

OTHER PUBLICATIONS

Experian Information Solutions, Inc., "Instant Prescreen", 2000 [online] [retrieved on Aug. 11, 2005] Retrieved from the Internet <URL:http://www.cdillinois.com/pdf_file/instant_prescreen_ps.pdf>.

(Continued)

*Primary Examiner* — Asfand Sheikh
(74) *Attorney, Agent, or Firm* — Knobbe, Martens, Olson & Bear, LLP

(57) ABSTRACT

In one embodiment, prescreened credit card offers, which are associated with credit cards that a particular borrower would be accepted upon application with the respective issuer, are provided to a borrower via a prescreen provider website and/or a referrer website. In one embodiment, a referrer provides borrower information to a prescreen provider. The prescreen provider initiates and/or performs a prescreening process, which includes accessing credit related information regarding the borrower. The prescreen provider matches the borrower with one or more credit cards that the borrower would like be accepted for, and provides a prescreened offer document to the referrer, or an Internet address of the prescreened offer document. The referrer may then provide the borrower with the prescreened credit card offers by presenting the prescreened offer document to the borrower. The prescreened credit card offers may additionally be filtered according to issuer criteria, referrer criteria, and/or borrower preferences.

20 Claims, 16 Drawing Sheets

U.S. PATENT DOCUMENTS

| | | | |
|---|---|---|---|
| 5,970,478 | A | 10/1999 | Walker et al. |
| 5,978,785 | A | 11/1999 | Johnson et al. |
| 5,995,947 | A | 11/1999 | Fraser et al. |
| 6,029,149 | A | 2/2000 | Dykstra et al. |
| 6,088,686 | A | 7/2000 | Walker et al. |
| 6,129,273 | A | 10/2000 | Shah |
| 6,144,948 | A | 11/2000 | Walker et al. |
| 6,158,657 | A | 12/2000 | Hall et al. |
| 6,185,543 | B1 | 2/2001 | Galperin et al. |
| 6,374,230 | B1 | 4/2002 | Walker et al. |
| 6,385,594 | B1 | 5/2002 | Lebda et al. |
| 6,405,181 | B2 | 6/2002 | Lent et al. |
| 6,611,816 | B2 | 8/2003 | Lebda et al. |
| 6,640,215 | B1 | 10/2003 | Galperin et al. |
| 6,980,969 | B1 * | 12/2005 | Tuchler et al. ............ 705/39 |
| 7,178,720 | B1 * | 2/2007 | Strubbe et al. ............ 235/375 |
| 7,337,468 | B2 * | 2/2008 | Metzger ............ 726/6 |
| 7,379,913 | B2 | 5/2008 | Steele et al. |
| 2002/0004735 | A1 | 1/2002 | Gross |
| 2002/0040339 | A1 * | 4/2002 | Dhar et al. ............ 705/38 |
| 2002/0072975 | A1 | 6/2002 | Steele et al. |
| 2002/0077964 | A1 | 6/2002 | Brody et al. |
| 2002/0099641 | A1 | 7/2002 | Mills et al. |
| 2002/0194103 | A1 | 12/2002 | Nabe |
| 2003/0078877 | A1 | 4/2003 | Beirne et al. |
| 2003/0144907 | A1 | 7/2003 | Cohen, Jr. et al. |
| 2003/0208412 | A1 | 11/2003 | Hillestad et al. |
| 2004/0054619 | A1 | 3/2004 | Watson et al. |
| 2004/0064402 | A1 | 4/2004 | Dreyer et al. |
| 2004/0215556 | A1 | 10/2004 | Merkley, Jr. et al. |
| 2005/0065874 | A1 | 3/2005 | Lefner et al. |
| 2005/0137939 | A1 | 6/2005 | Calabria et al. |
| 2005/0159993 | A1 | 7/2005 | Kordas et al. |
| 2005/0187860 | A1 | 8/2005 | Peterson et al. |
| 2005/0209922 | A1 | 9/2005 | Hofmeister |
| 2005/0228748 | A1 | 10/2005 | Togher et al. |
| 2005/0279830 | A1 * | 12/2005 | Chao ............ 235/380 |
| 2006/0080233 | A1 | 4/2006 | Mendelovich et al. |
| 2006/0080251 | A1 | 4/2006 | Fried et al. |
| 2006/0095363 | A1 | 5/2006 | May |
| 2006/0100954 | A1 | 5/2006 | Schoen |
| 2006/0155639 | A1 | 7/2006 | Lynch et al. |
| 2006/0173772 | A1 | 8/2006 | Hayes et al. |
| 2006/0178983 | A1 | 8/2006 | Nice et al. |
| 2008/0059317 | A1 | 3/2008 | Chandran et al. |
| 2008/0059352 | A1 | 3/2008 | Chandran |
| 2008/0065569 | A1 | 3/2008 | Dutt et al. |

OTHER PUBLICATIONS

Experian Global Press Office, "Experian Enables Profitable e-Business", 2000 [online] [retrieved on Aug. 11, 2005] Retrieved from the Internet <URL:http://press.experian.com/popup/sd.cfm?f=43.htm>.

Experian Global Press Office, "Experian Announces Innovative e-Commerce Technology Enhancement", 2001 [online] [retrieved on Aug. 11, 2005] Retrieved from the Internet <URL:http://press.experian.com/popup/sd.cfm?f=280.htm >.

Experian Information Solutions, Inc., "Enabling e-business", 2001 [online] [retrieved on Aug. 11, 2005] Retrieved from the Internet <URL:http://press.experian.com/documents/enablingebusiness.pdf >.

Fairlsaac, "Case Study: Expanding to Non-Traditional Prescreen Marketing Channels Reduces Company's Cost Per Account Booked", 2003 [online] [retrieved on Sep. 1, 2005] Retrieved from the Internet <URL:http://www.fairisaac.com/NR/rdonlyres/048FAE87-14B5-4732-970D-BDF20F09EB2D/0/MSDSRealTimeCS.pdf>.

Office Action dated Jul. 28, 2008 in co-pending U.S. Appl. No. 11/219,142.

Office Action dated Jun. 15, 2009 in co-pending U.S. Appl. No. 11/219,142.

Office Action dated Jan. 22, 2010 in co-pending U.S. Appl. No. 11/219,142.

Office Action dated Sep. 13, 2010 in co-pending U.S. Appl. No. 11/219,142.

Office Action dated Oct. 10, 2008 in co-pending U.S. Appl. No. 11/848,138.

Office Action dated Sep. 25, 2009 in co-pending U.S. Appl. No. 11/848,138.

Office Action dated Feb. 4, 2010 in co-pending U.S. Appl. No. 11/848,138.

* cited by examiner

Quick Match

Submit your info and see what cards match your profile.

First Name:

Last Name:

Home Address:

City:

State: Select

Zip Code:

[Click to Submit]

800

810

812

---

Browse by Card Type:
Select One
[Go]

Browse by Bank:
Select One
[Go]

Card Categories:
- All Cards
- 0% Intro APR
- Instant Approval
- Rewards
- Poor Credit
- Cash Back
- Student
- Business
- Popular
- Gold or Platinum Status
- Airline and Hotel Rewards
- Shopping Rewards

820

822

My credit profile is...
Excellent

My most desired card benefit is...
Select One

My occupational status is...
Select One

[Click Here To Start]

Congratulations! We found your match. Step: 1 2 3 4

Based on your profile you are pre-approved for 4 credit cards.

Match 1 of 4:

You're Pre-Approved!

Citi® Platinum Select® Card

| Interest Rate | Intro Rate | Grace Period | Credit Limit | Annual Fee |
|---|---|---|---|---|
| 9.24% | 0% | 20 Days | No Limit | $10 |

Our Overview
0% on Balance Transfers & Purchases for 12 months. NO Balance Transfer fee, NO annual fee. Plus, access to Citi® Identity Theft Solutions, $0 Liability on unauthorized purchases and Secure, free online account management.

- Credit line up to $100,000 with Platinum Select® Card
- Introductory 0% Annual Percentage Rate (APR) for cash advance checks and balance transfers through your first twelve billing cycles.*
- Zero liability for unauthorized card use **
- Earn reward points to redeem airline and car rental benefits as well as gift certificate/cards redeemable at top retailer and restaurants.

▶ Click Here To Get Your Card Now — 910

No thanks, pass this offer and show me the next credit card I'm pre-approved for. — 920

Congratulations! We found your match. Steps: 1 2 3 4

Based on your profile you are pre-approved for 4 credit cards.

Match 2 of 4:

You're Pre-Approved!

Discover® Platinum Select® Card

| Interest Rate | Intro Rate | Grace Period | Credit Limit | Annual Fee |
|---|---|---|---|---|
| 9.24% | 0% | 20 Days | No Limit | $10 |

Our Overview
0% on Balance Transfers & Purchases for 12 months. NO Balance Transfer fee, NO annual fee. Plus, access to Citi® Identity Theft Solutions, $0 Liability on unauthorized purchases and Secure, free online account management.

▶ Click Here To Get Your Card Now — 1010

No thanks, pass this offer and show me the next credit card I'm pre-approved for. — 1020

- Credit line up to $100,000 with Platinum Select® Card
- Introductory 0% Annual Percentage Rate (APR) for cash advance checks and balance transfers through your first twelve billing cycles.*
- Zero liability for unauthorized card use.\*\*
- Earn reward points to redeem airline and car rental benefits as well as gift certificate/cards redeemable at top retailer and restaurants.

Congratulations! We found your match.   Step: 1 2 3 4

You're Pre-Approved!

Based on your profile you are pre-approved for these 3 credit cards.

| Card Name | Citi® Platinum Select® | Citi® Drivers Edge® Card | Citi® Student Edge® Card |
|---|---|---|---|
| | Click to Apply | Click to Apply | Click to Apply |
| Interest Rate | 9.24% | 10.24% | 9.24% |
| Intro Rate | 0% | 0% | 0% |
| Grace Period | 20 Days | 20 Days | 20 Days |
| Credit Limit | No Limit | No Limit | No Limit |
| Annual Fee | None | None | None |
| Our Overview | 0% on Balance Transfers & Purchases for 12 months. NO Balance Transfer fee, NO annual fee. Plus, access to Citi® Identity Theft Solutions, $0 Liability on unauthorized purchases and Secure, free online account management. | 0% on Balance Transfers & Purchases for 12 months. NO Balance Transfer fee, NO annual fee. Plus, access to Citi® Identity Theft Solutions, $0 Liability on unauthorized purchases and Secure, free online account management. | 0% on Balance Transfers & Purchases for 12 months. NO Balance Transfer fee, NO annual fee. Plus, access to Citi® Identity Theft Solutions, $0 Liability on unauthorized purchases and Secure, free online account management. |

No thanks, pass on these offers and show me other credit cards I might be interested in

Figure 11

Tell us how you plan on using the card.   Step 1 [2] 3 4

18 credit cards match your current profile
Answer these simple questions and we can narrow it down even more.

My current balance is paid in full each month...   ⦿ Yes ○ No

My primary checking or savings account is....   Bank of America (These questions are Optional)

Go Back   (▲) Continue

Top Credit Card Matches

Discover® Platinum Clear Card
Interest Rate  Intro Rate  Grace Period  Annual Fee
10.99% +    0.0%       25 Days      None
Overview: ⊞

Click to Apply

Elite Rewards® World MasterCard® from Bank of America
Interest Rate  Intro Rate  Grace Period  Annual Fee
7.9% +      0.0%       20 Days      None
Overview: ⊞

Click to Apply

See all 18 credit cards match your current profile

FIGURE 12

ONLINE CREDIT CARD PRESCREEN SYSTEMS AND METHODS

This application claims priority under 35 U.S.C. §119(e) to U.S. Provisional Application Ser. No. 60/824,258 and to U.S. Provisional Application Ser. No. 60/824,252, each of which were filed on Aug. 31, 2006, and each of which are hereby expressly incorporated by reference in their entireties.

BACKGROUND OF THE INVENTION

1. Field of the Invention

This invention relates to systems and methods of prescreening a potential borrower for one or more credit card offers, or offers for other financial instruments.

2. Description of the Related Art

Lending institutions provide credit accounts such as mortgages, automobile loans, credit card accounts, and the like, to consumers. Prior to providing an account to a potential borrower, or borrowers, however, many of these institutions review credit related data, demographic data, and/or other data related to the potential borrower in order to determine whether the borrower should be issued the applied-for credit account. In the case of credit cards, for example, credit card issuers typically obtain a credit report for the potential borrower in order to aid in determining whether the borrower should be offered a credit card and, if so, what rates and terms should be offered to the borrower. Thus, for any particular credit card, a first group of borrowers will be accepted for the credit card and a second group of borrowers will not be accepted for the credit card, where the size of the accepted group typically increases as the desirability of the credit card decreases.

Credit card issuers often send direct mail to potential borrowers, including invitations to apply for one or more of the respective issuer's credit cards. In some cases, characteristics of potential borrowers, such as credit related information, are reviewed in order to determine which borrowers should be sent the credit card offer. The potential borrower may respond to the invitation to apply by filling out a credit card application and mailing the application to the issuer. However, this process may take weeks, or even months, from the time the issuer decides to send the offer to the borrower until the time the borrower completes and returns the credit card application. Additionally, the received invitation to apply is from a single credit card issuer and, thus, any comparison of the offered credit card to credit cards from other issuers is done by the borrower.

SUMMARY

In one embodiment, a method of prescreening a potential borrower for each of a plurality of credit card offers is described, wherein the plurality of credit card offers comprises at least a first credit card offer associated with a first lender and a second credit card offer associated with a second lender. The method comprises presenting a browser-viewable document to a borrower, the browser-viewable document comprising information entry fields for entry of borrower information by the borrower, wherein the borrower information comprises a first name, a last name, and one or more of: a street address, a city, a state, and a zip code, receiving the borrower information via one or more networks, transmitting the borrower information to a prescreened offer source configured to access credit data related to the borrower and determine zero or more prescreened credit card offers indicating credit cards that the borrower would likely be accepted for by the respective issuer, and receiving from the prescreened offer source information regarding the zero or more prescreened credit card offers, applying at least one filter to each of the prescreened credit card offers, the at least one filter selected from the group comprising: a filter comprising geographic criteria, a filter comprising issuer criteria, a filter comprising borrower preferences. In one embodiment, if one or more prescreened credit card offers are received, the method comprises generating a browser-viewable prescreened offer document comprising information regarding at least one of the prescreened credit card offers, the prescreened offer document comprising a link associated with each prescreened offer, wherein the links are associated with a browser-viewable documents that allows the borrower to apply for the respective prescreened offers. In one embodiment, if zero prescreened credit card offers are received, the method comprises generating a browser-viewable invitation to apply document comprising information regarding one or more invitations to apply for credit cards, and presenting the invitation to apply document to the borrower.

In another embodiment, a method of determining whether a borrower's application for each of a plurality of credit card offers will likely be accepted by respective issuers of the credit cards in response to application for the respective credit card by a borrower is described. In one embodiment, the method comprises receiving from a referrer a request to provide one or more prescreened credit card offers to a borrower, determining a first subset of the plurality of credit card offers, wherein the first subset comprises credit card offers that have been selected by the referrer, transmitting a prescreening request to a prescreened offer source, the prescreening request comprising information regarding the borrower, receiving a second subset of credit card offers from the prescreened offer source, wherein the second subset comprises credit card offers from the first subset that are likely to be granted by an issuer associated with the respective credit card offers, ranking the second subset of credit card offers based at least partly on a fee paid by the respective issuer for presenting the borrower with information regarding the respective credit card offers; and transmitting information regarding at least a highest ranked credit card offer to the referrer.

In another embodiment, a prescreening system comprises a user interface that is viewable by a computing device in communication with the Internet, the user interface comprising one or more criteria fields associated with characteristics of credit cards, wherein in response to selection of criteria in the one or more criteria fields, the user interface is updated with information regarding one or more invitations to apply for credit card offers that match the selected criteria, a prescreen module for receiving borrower information entered into the user interface via the computing device, a prescreened offer source for accessing credit data associated with the borrower information and determining, based at least on the credit data, one or more credit cards for which the borrower would likely be accepted, and a presentation module for generating a document comprising information regarding the one or more credit cards.

In another embodiment, a method of providing one or more prescreened credit card offers to a borrower via a third party referrer website comprises receiving borrower information from a referrer, the referrer operating a referrer website, determining one or more credit card offers for which the borrower would likely be accepted, generating a prescreened offer document identifying the one or more credit card offers and providing a location of the prescreened offer document to the third party.

In another embodiment, a method of presenting one or more prescreened credit card offers to a customer comprises receiving customer information regarding the customer, the customer information comprising one or more of a first name, last name, residence address, city, state, and zip code, transmitting the customer information to a prescreen provider, receiving from the prescreen provider a location of a prescreened offer document, the prescreened offer document identifying one or more credit card offers for which the customer would likely be accepted and presenting the prescreened offer document to the customer.

BRIEF DESCRIPTION OF THE DRAWINGS

FIG. 8 is one embodiment of a screenshot of a user interface that allows a potential borrower to enter information for submission to a prescreen provider.

FIG. 9 is one embodiment of a screenshot of a user interface presenting a first credit card offer for which a borrower has been pre-approved.

FIG. 10 is one embodiment of a screenshot of a user interface presenting a second credit card offer for which the borrower has been pre-approved.

FIG. 11 is one embodiment of a screenshot of a user interface concurrently presenting multiple credit card offers for which a borrower has been pre-approved.

FIG. 12 is one embodiment of a screenshot of a second user interface requesting additional information from the borrower.

DETAILED DESCRIPTION OF CERTAIN EMBODIMENTS

Embodiments of the invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions described herein.

The systems and methods described herein generally perform a prescreening process on a potential borrower in order to determine which credit card or credit cards the borrower will likely be issued after completing a full application with the issuer. The term "borrower," as used herein means a single individual, a group of people, such as a couple or a family, a business, or other entity. The terms "prescreened credit card offers," or simply "prescreened offers," refer to credit card offers for which a potential borrower will likely be approved by the issuer, where the prescreening process may be based on credit data associated with the borrower, as well as approval criteria for respective credit cards, credit card issuer criteria, and/or any other relevant criteria. A borrower is said to be "matched" to each credit card offer that is returned from a prescreened offer source and passed through one or more filters by a prescreen provider. Thus, the borrower may be matched to zero, one, two, or any number of credit cards, depending on the results of the prescreening process and the filters applied by the prescreen provider. In one embodiment, the prescreened offers presented to a particular borrower are accepted by the respective credit card issuers at a higher rate than non-prescreened credit card offers selected by the borrower. For example, more than 90% of applications for credit cards indicated in prescreened credit card offers may be accepted by their respective issuers. In other embodiments, the acceptance percentage for prescreened offers may be higher or lower than 90%, such as 60%, 72.5%, 80%, or 95%, for example.

Figure 1:
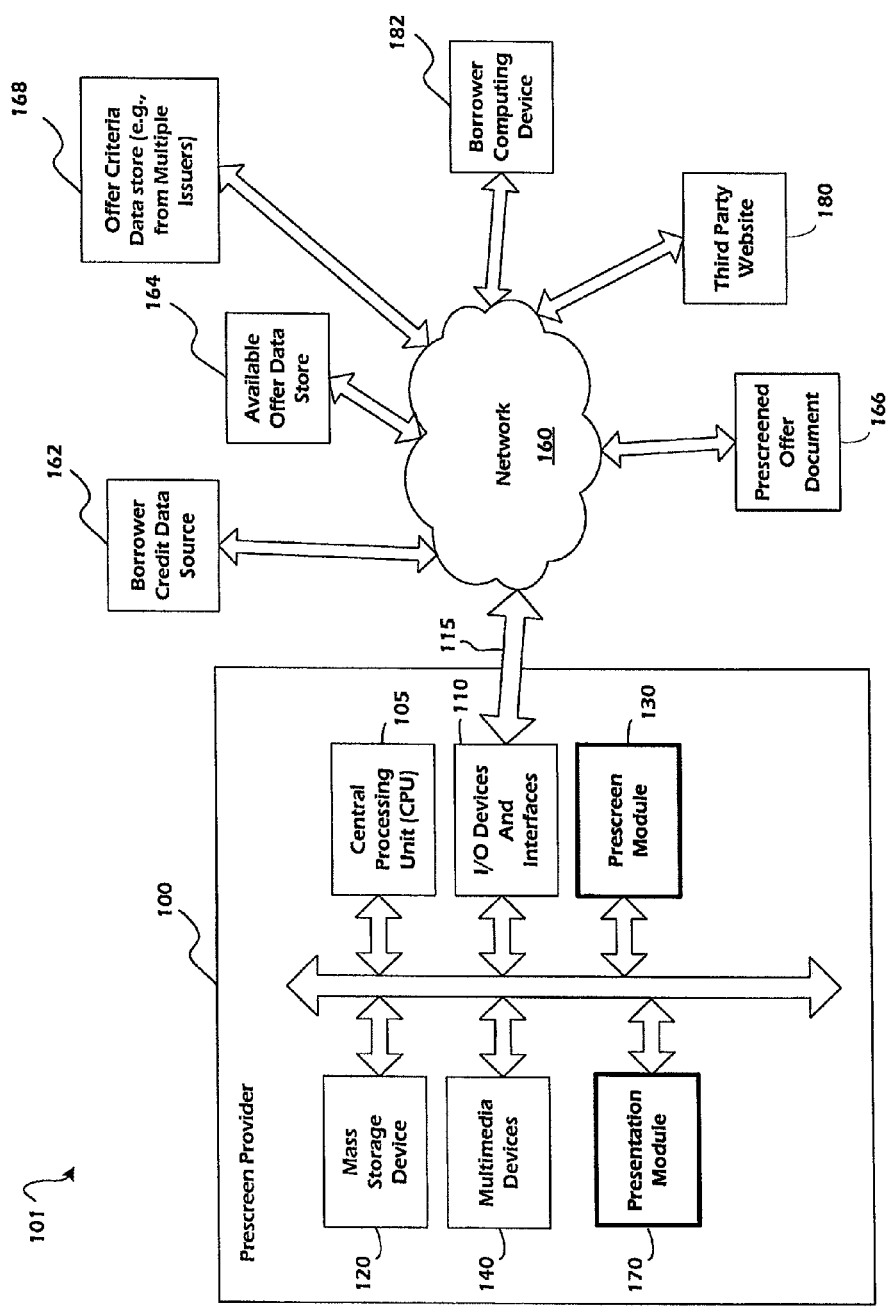
FIG. 1 is a block diagram of one embodiment of a prescreen system configured to match a borrower to credit card offers.

FIG. 1 is a block diagram of a first embodiment of a prescreen system 101 comprising a prescreen device 100 configured to match a borrower to credit cards offers. In one embodiment, the prescreen device 100 is controlled and/or operated by a "prescreen provider." The exemplary prescreen device 100 is in communication with a network 160. Various additional devices and data sources are also in communication with the network 160. More particularly, in the embodiment of FIG. 1, a borrower credit data source 162, an available offer data store 164, an offer criteria data store 168, a prescreened offer document 166, a third party website 180, and a borrower computing device 182, such as a personal computer, are each in communication with the network 160. In different embodiments, the borrower computing device 182 comprises a desktop computer, a laptop computer, a cell phone, a personal digital assistant, a kiosk, or an audio player, for example. In other embodiments, any of the networked components may be directly coupled to, or maintained on, the prescreen device 100. For example, in one embodiment the offer criteria data store 168 and the available offer data store 164, and/or copies of these data stores, are stored on the prescreen device 100.

The prescreen device 100 may be used to implement certain systems and methods described herein. For example, in one embodiment the prescreen device 100 may be configured to prescreen potential borrowers, also referred to herein simply as "borrowers," in order to match the borrower with one or more credit card offers, and to present one or more of the prescreened offers to the borrower via the prescreened offer document 166. In an advantageous embodiment, the prescreened offer document 166 comprises a document, such as an HTML document or e-mail, that is viewable in a web browser or other software that is running on the borrower computing device 182. The functionality provided for in the components and modules of the prescreen device 100 may be combined into fewer components and modules or further separated into additional components and modules. For example, the prescreen device 100 may comprise multiple central processing units (CPUs) and a mass storage device, such as may be implemented in an array of servers.

In general, the word "module", as used herein, refers to logic embodied in hardware or firmware, or to a collection of software instructions, possibly having entry and exit points, written in a programming language, such as, for example, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

In one embodiment, the prescreen device 100 includes, for example, a computing device that is IBM, Macintosh, or Linux/Unix compatible. In another embodiment, the prescreen device 100 comprises a laptop computer, a cell phone, a personal digital assistant, a kiosk, or an audio player, for example. In one embodiment, the exemplary prescreen device 100 includes one or more CPUs 105, which may each include microprocessors. The prescreen device 100 may further include one or more memory devices, such as random access memory (RAM) for temporary storage of information and read only memory (ROM) for permanent storage of information, and one or more mass storage devices 120, such as hard drives, diskettes, or optical media storage devices. In one embodiment, the modules of the prescreen device 100 are in communication via a standards based bus system, such as bus systems using Peripheral Component Interconnect (PCI), Microchannel, SCSI, Industrial Standard Architecture (ISA) and Extended ISA (EISA) architectures, for example. In certain embodiments, components of the prescreen device 100 communicate via a network, such as a local area network that may be secured.

The prescreen device 100 is generally controlled and coordinated by operating system software, such as the Windows 95, Windows 98, Windows NT, Windows 2000, Windows XP, Windows Vista, Linux, SunOS, Solaris, PalmOS, Blackberry OS, or other compatible operating systems. In Macintosh systems, the operating system may be any available operating system, such as MAC OS X. In other embodiments, the prescreen device 100 may be controlled by a proprietary operating system. Conventional operating systems control and schedule computer processes for execution, perform memory management, provide file system, networking, and I/O services, and provide a user interface, such as a graphical user interface ("GUI"), among other things.

The exemplary prescreen device 100 includes one or more commonly available input/output (I/O) devices and interfaces 110, such as a keyboard, mouse, touchpad, microphone, and printer. Thus, in one embodiment the prescreen device may be controlled using the keyboard and mouse input devices, while in another embodiment the user may provide voice commands to the prescreen device via a microphone. In one embodiment, the I/O devices and interfaces 110 include one or more display device, such as a monitor, that allows the visual presentation of data to a user. More particularly, a display device provides for the presentation of GUIs, application software data, and multimedia presentations, for example. The prescreen device 100 may also include one or more multimedia devices 140, such as speakers, video cards, graphics accelerators, and microphones, for example.

In the embodiment of FIG. 1, the I/O devices and interfaces 110 provide a communication interface to various external devices. In the embodiment of FIG. 1, the prescreen device 100 is in communication with a network 160, such as any combination of one or more LANs, WANs, or the Internet, for example, via a wired, wireless, or combination of wired and wireless, communication link 115. The network 160 communicates with various computing devices and/or other electronic devices via wired or wireless communication links.

In the embodiment of FIG. 1, a borrower credit data source 162 is in communication with the network 160. In one embodiment, the borrower data source 162 is maintained by a credit bureau or other entity that provides credit reports. For example, the borrower data source 162 may comprise data that is maintained by Experian, Equifax, or Trans-Union. An available offer database 164 is also in communication with the network 160. In one embodiment, the available offer database comprises a list of credit cards for which a borrower may apply. The available offer database 164 may be continually and/or periodically updated by credit card issuers in order to include the currently available credit card offers. In the embodiment of FIG. 1, an offer criteria data store 168 is also in communication with the network 160. In one embodiment, the available offer database 164 and the offer criteria database 168 are maintained by the same entity, such as, for example, a credit bureau or the entity operating the prescreen device 100, which is referred to herein as the "prescreen provider." In one embodiment, the offer criteria data store 168 comprises one or more criteria for matching borrowers to respective credit cards. Thus, in order for a borrower to be matched to a particular credit card, the credit data associated with the borrower must satisfy the criteria for the particular credit card indicated in the offer criteria data store 168. In one embodiment, the offer criteria data store 168 receives criteria from a plurality of credit card issuers, where each credit card issuer has issuer specific criteria and/or credit card specific criteria.

In one embodiment, a third-party website 180 is also in communication with the network 160. In one embodiment, the third party website 180 is operated and/or controlled by a "referrer," which is defined herein to mean an entity that provides credit card offers to potential borrowers. Thus, in the embodiment of FIG. 1 a referrer operates and/or controls the third party website, which may be used to display prescreened offers to potential borrowers that access the website 180. In one embodiment, the third-party website 180 is accessed by a potential borrower via the borrower computing device 182, for example, and the third-party website 180 provides the borrower's information to the prescreen device 100 in order to acquire prescreened credit card offers for the borrower.

A prescreened offer document 166 comprises a list of one or more prescreened credit card offers for a particular borrower. Accordingly, for each borrower on which a prescreen process is performed, a different prescreened offer document 166 may be generated by the prescreen device 100 and, more specifically, by the presentation module 170. The prescreened offer document 166 may be in any format, such as an HTML document, an XML document, an e-mail, or a printed document that may be sent by snail mail, for example. In one embodiment, the prescreen device 100 generates an Internet-accessible prescreened offer document 166, such as an HTML document, that may be displayed in a prescreen provider website or that may be provided to the third-party website 180. In one embodiment, an address of the prescreened offer document 166, such as a uniform resource locator ("URL") of the prescreened offer document 166 is provided to the third party website 180, or other referrer, so that the third-party website 180 can present the matched credit card offers to the borrower simply by directing the borrower to the pre-created prescreened offer document 166.

In the embodiment of FIG. 1, the prescreen device 100 also includes two application modules that may be executed by the CPU 105. More particularly, the application modules include a prescreen module 130 and a presentation module 170, which are discussed in further detail below. Each of these application modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. In the embodiments described herein, the prescreen device 100 is configured to execute the prescreen module 130 and/or the presentation module 170, among others, in order to provide a list of prescreened credit card offers and generate a prescreened offer document, which may be electronic or non-electronic, for a particular borrower. In general, the prescreen module 130 coordinates the prescreening process, such as the exemplary prescreening processes described below with reference to FIG. 2. In other embodiments, the prescreen module 130 also performs a prescreening process, such as the process described with reference to FIG. 3 and/or a filtering process, such as the process described with reference to FIG. 5, in addition to other processes. The presentation module 170 receives the prescreened credit card offers for a borrower and presents the offers to the borrower in one of several formats, such as by using the process described with reference to FIG. 5, for example.

Figure 1A:
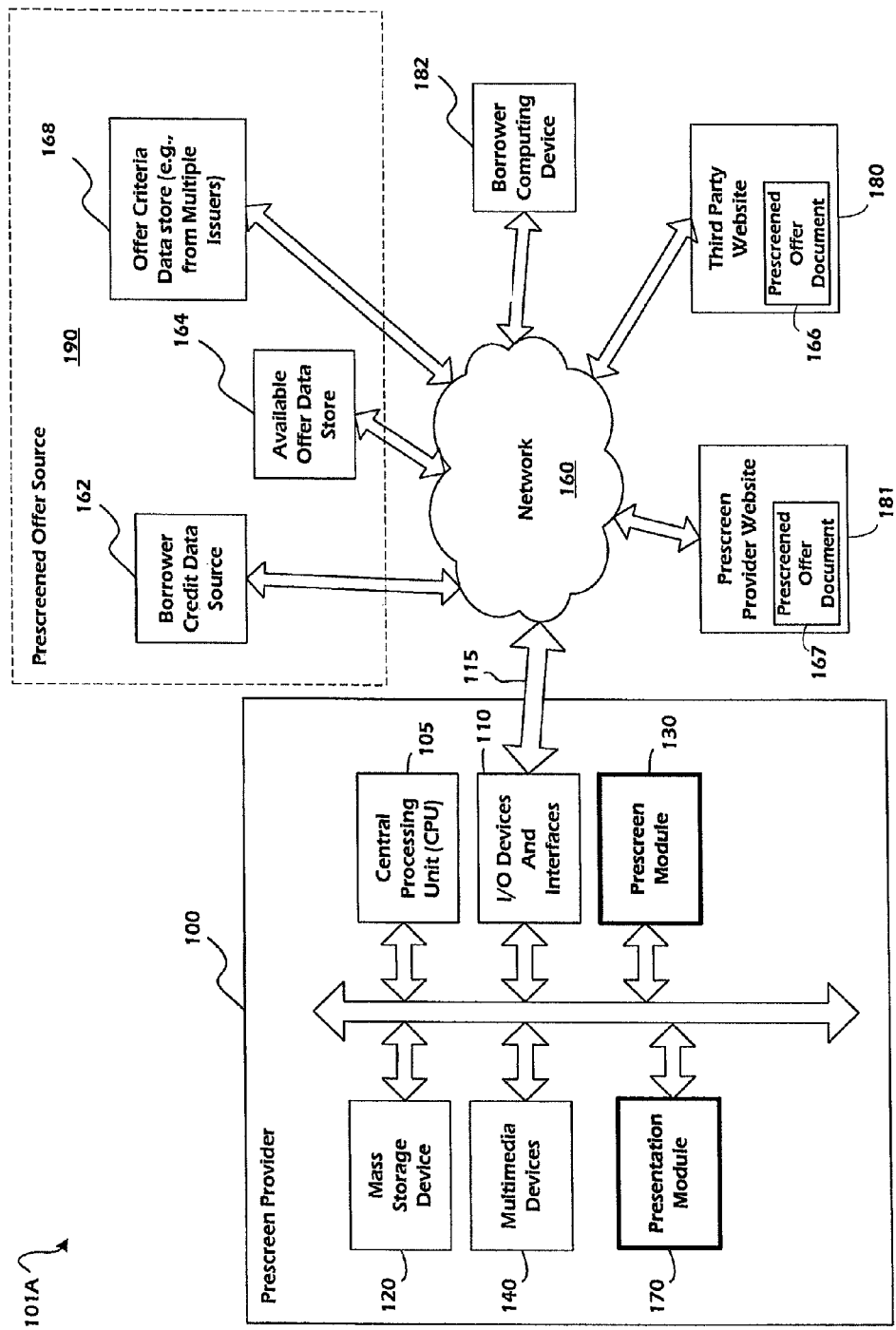
FIG. 1A is a block diagram of another embodiment of a prescreen system, wherein certain of the modules in communication with the network are combined within a prescreened offer source and a prescreen provider website is in communication with the network.

FIG. 1A is a block diagram of another embodiment of a prescreen system 101A, wherein certain of the modules in communication with the network are combined within a prescreened offer source 190. More particularly, in this embodiment the borrower credit data source 162, the available offer data store 164, and the offer criteria data store 168 are each part of a prescreened offer source 190. In one embodiment, the prescreened offer source 190 is controlled and/or operated by the prescreen provider and the prescreen module 130 may comprise the prescreened offer source 190, for example. In another embodiment, the prescreened offer source is controlled and/or operated by a credit bureau, such as Experian, Equifax, or Transunion, for example. In another embodiment, the prescreened offer source 190 is controlled and/or operated by an agent of a credit bureau, such as Experian-Scorex. In this embodiment, the prescreened offer source 190 may provide a list of prescreened offers to the prescreen device 100 via the network 160 in response to receiving borrower information from the prescreen device 100. More particularly, the prescreened offer source 190 may access the borrower's credit data and compare the credit data to the offer criteria stored in the offer criteria data store 168 in order to generate a list of prescreened credit card offers for the borrower. In one embodiment, the list of prescreened offers, or the list of credit card offers listed in the available offer data store 164, may be narrowed based on preferences of the issuer, borrower, or referrer, for example, such as a subset of credit card offers that a referrer wants to provide to their customers. Thus, in one embodiment the prescreened offer source 190 performs a prescreening process, such as the exemplary prescreening process of FIG. 3.

In the embodiment of FIG. 1A, the prescreen system 101A comprises a prescreened provider website 181 in communication with the network 160. In one embodiment, the prescreened provider website 181 comprises a website that is configured to receive information from a borrower and provide the borrower with prescreened credit card offers, and/or invitations to apply ("ITA") for credit card offers. In one embodiment, ITAs for one or more credit cards are presented to borrowers when the prescreening process returns zero prescreened offers for the borrower. As shown in FIG. 1A, the prescreened provider website 181 comprises the prescreened offer document 181, which may be displayed as a part of the website. Thus, the prescreen provider may receive borrower information, prescreen the borrower in order to determine zero or more prescreened offers, and then present the prescreened offers to the borrower in the form of the prescreened offer document 166. FIG. 8 illustrates one example of a user interface that may be presented to a borrower as part of the prescreen provider website 181.

Figure 1B:
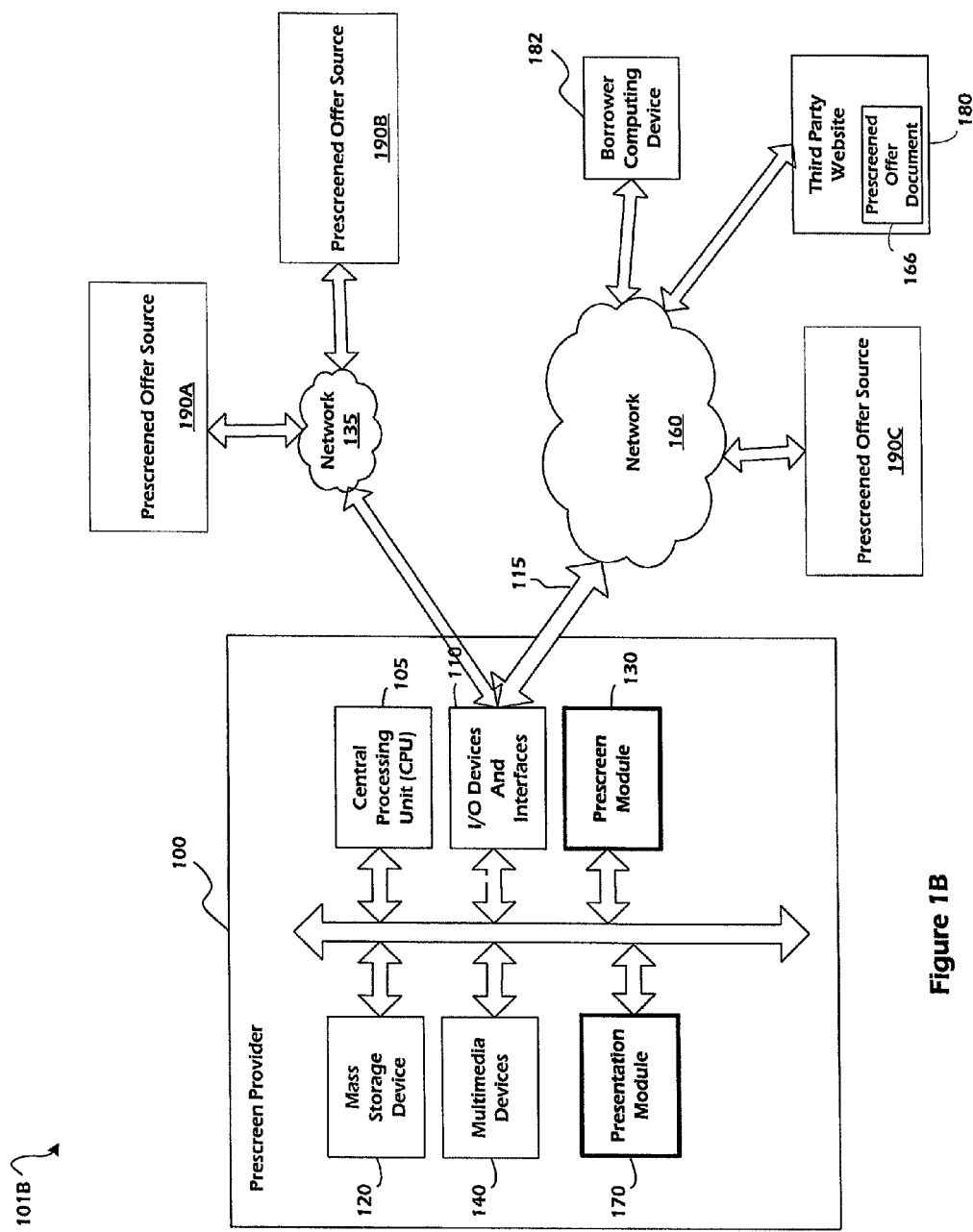
FIG. 1B is a block diagram of another embodiment of a prescreen system, wherein one or more prescreened offer sources are in communication with the prescreen device via a secured network.

FIG. 1B is a block diagram of another embodiment of a prescreen device 101B, wherein two prescreened offer sources 190A, 190B are in communication with the prescreen device 100 via a secured network 135 and a third prescreened offer source 190C is in communication with the prescreen device 100 via the network 160. In one embodiment, one or more of the prescreened offer sources 190A, 190B, 190C comprises a credit bureau, such as Experian, Equifax, or Transunion. In another embodiment, one or more of the prescreened offer sources 190A, 190B, 190C access a credit bureau in order to obtain credit information for the borrower, which may be used in identifying any prescreened offers that should be returned to the prescreen device 100. In one embodiment, one or more of the prescreened offer sources 190 comprises only the borrower credit data source 162, for example. Thus, in one embodiment borrower credit data may be accessed from multiple borrower credit data sources 162 of prescreened offer sources 190, while the available offer data store 164 and offer criteria 168 may be accessed from a single prescreened offer source 190.

In the embodiment of FIG. 1B, the network 135 comprises a private and/or secured network that is not accessible to the general public. For example, the network 135 may comprise a LAN that is secured by a hardware and/or software firewall. In the embodiment of FIG. 1B, multiple prescreened offer sources 190 are in communication with the prescreen device 100 and may each provide prescreened offers to the prescreen device 100. In one embodiment, the prescreened offer sources 190 may each comprise different available credit card offers, along with the corresponding offer criteria for the credit card offers. Thus, by accessing multiple prescreened offer sources 190, the prescreen device 100 may match borrowers to increased numbers of credit card offers. Accordingly, in one embodiment the prescreen device 100 requests prescreened offers from two or more prescreened offer sources 190 and presents prescreened offers to the borrower that were returned from multiple prescreened offer sources 190. Additionally, in certain embodiments a third party referrer, such as the operator of the third party website 180, may request that credit card offers are obtained from a particular one or more prescreened offer sources 190. Thus, in one embodiment the prescreen device 100 request prescreened offers from the one or more prescreened offer sources 190 specified by the referrer.

Figure 2:
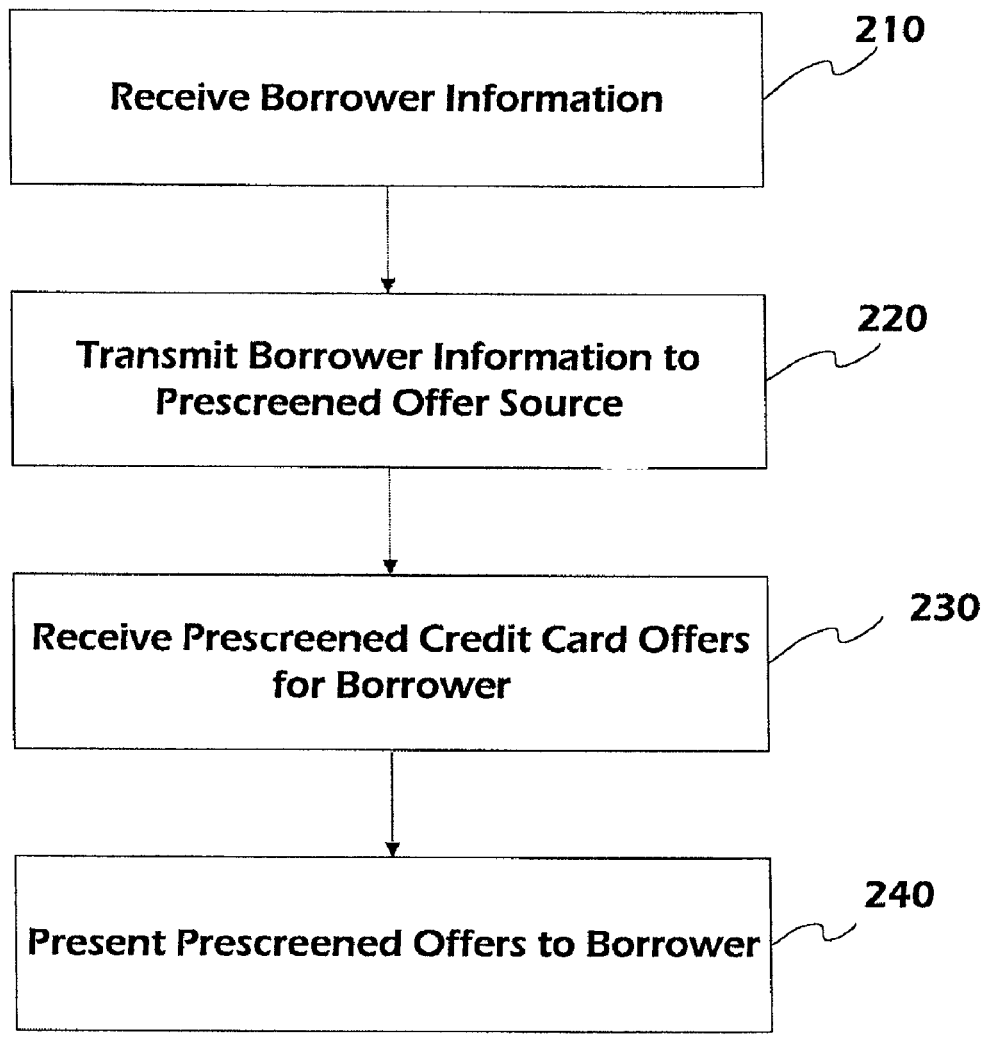
FIG. 2 is a flowchart illustrating one embodiment of a prescreening method.

FIG. 2 is a flowchart illustrating an exemplary process that may be performed by the prescreen device 100 (FIG. 1) in order to match a borrower to one or more credit card offer. Depending on the embodiment, certain of the blocks described below may be removed, others may be added, and the sequence of the blocks may be altered. Additionally, although the following description describes that the prescreen device 100 performs the methods of FIG. 2, in some embodiments one or more of the blocks may be performed by other devices, such as by a prescreened offer source 190. The exemplary embodiments below are described generally with respect to a system comprising a single prescreened offer source 190, such as illustrated in FIG. 1A, for example. However, any of the embodiments described herein may be performed using any one or more of the prescreened offer sources 190, such as those illustrated in FIG. 1B, for example.

As noted above, communication between the multiple components illustrated in FIG. 1 may occur via the network 160, which may comprise the Internet, for example. Accordingly, a borrower or third party referrer may request that the borrower is prescreened, the prescreening process may be performed, and the borrower may be presented with the resultant prescreened credit card offers via multiple Internet based communications. Because the process is performed via computers networks, such as the Internet, the prescreened results may be substantially immediately provided to the borrower.

Beginning in a block 210, the prescreen module 130 (FIG. 1) of the prescreen device 100 receives, or otherwise accesses, information regarding a potential borrower. In one embodiment, the prescreen process may be provided using information entered into an Internet application running on the borrower computing device 182, or from any other Internet enabled devices, such as a third party Internet enabled computing device. In other embodiments, the borrower information may be received via non-Internet communications, such as on a portable storage device, for example a DVD or CD-ROM, that is mailed to the prescreen provider. In one embodiment, the Internet application executed by the borrower and/or one or more referrers that communicate with the prescreen device 100, comprises a web browser, such as Microsoft® Internet Explorer or Mozilla Firefox®, for example. Other Internet applications, such as custom application software, may also be used to transmit borrower data to the prescreen device 100 and to receive the link to the prescreened results.

In one embodiment, the prescreen module 130 may receive information, such as a name and address of a borrower, that has been entered into a website that is dedicated to matching consumers to prescreened credit card offers, such as the prescreen provider website 181 (FIG. 1A). In this embodiment, the borrower may enter data into a user interface that is provided by the prescreen provider, for example, specifically for the purpose of providing prescreened offers to the borrower. In another embodiment, an income level of the borrower and possibly additional information regarding the borrower is entered into the prescreen provider website 181 and used in determining prescreened offers for the borrower.

In another embodiment, some or all of the borrower information may be received from another data source, such as from a referrer. For example, in one embodiment a referrer operates the third party website 180, or another website, that may be either commercial or non-profit, such as may be operated by an educational institution. In one embodiment, the third party website 180 may be configured to sell any type of products and/or services to customers, or the website may be non-commercial. In this embodiment, the referrer may want to provide customers with credit card options in order to encourage increased purchases from the customers, for example. Accordingly, the referrer can send customer data to the prescreen device 100 in order in initiate a prescreening process and receive prescreened offers that may be presented to the customer, such as via the prescreened offer document 166. In another embodiment, a referrer may send a batch of customer data files to the prescreen device 100 and request prescreened offers for each of the customers. In this embodiment, the batch file may be transmitted in any manner, such as in an extensible markup language (XML) or comma separated values (CSV) file that is sent to the prescreen device 100 via an email or a file transfer protocol (FTP) server.

As noted above, in certain embodiments the referrer may receive a bounty upon issuance of the applied-for credit card to the borrower. Thus, if a referrer presents a prescreened credit card offer to a customer, such as via the prescreened offer document 166 (FIG. 1) that has been generated by the presentation module 170, the referrer may receive the corresponding bounty. Likewise, if the borrower information is received via a user interface operated by the prescreen provider, the bounty may be paid to the prescreen provider, rather than a third party referrer. In one embodiment, the referrer pays a fee to the prescreen provider for each prescreening that is performed, regardless of the number of prescreen offers that are presented in a resultant prescreened offer document 166. In another embodiment, the referrer pays the prescreen provider a fee that is based on the number and/or other characteristics of the prescreened offers included in the prescreened offer document 166. In one embodiment, the fees paid to the prescreen provider are also adjusted based on the prescreen offer source(s) 190 that are accessed by the prescreen device 100 and/or the number of prescreen offer sources 190 that are accessed.

Figure 3:
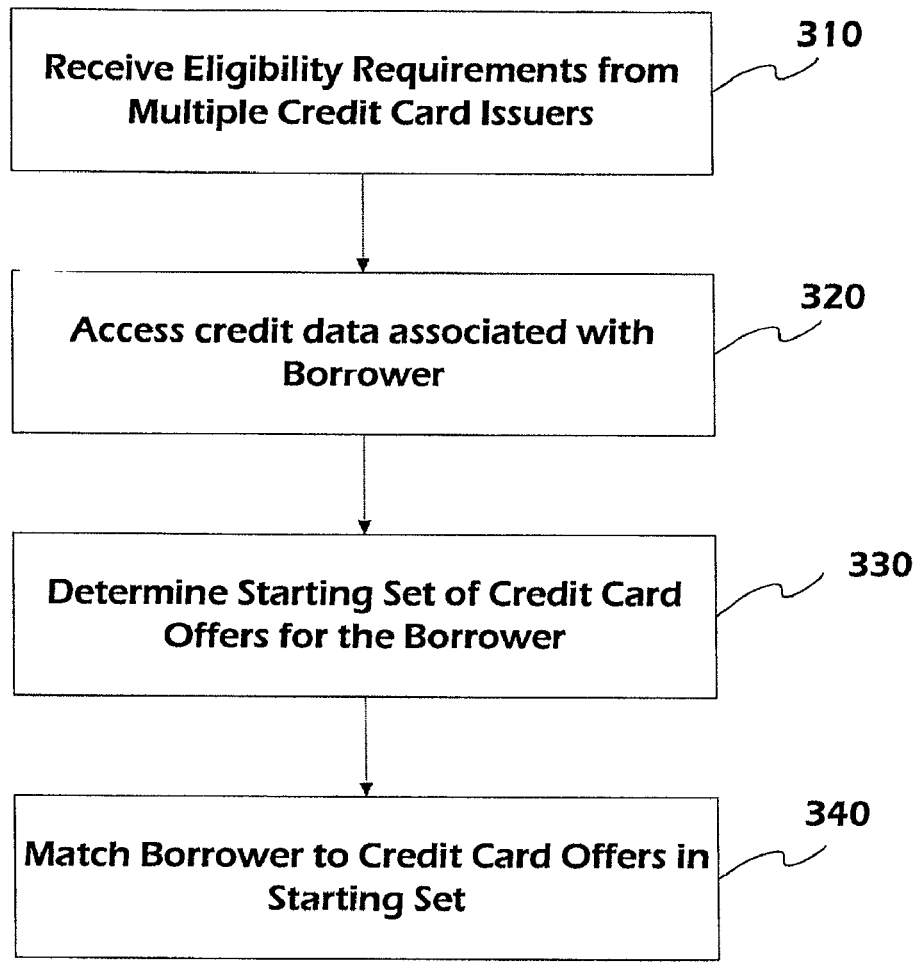
FIG. 3 is a flowchart illustrating one embodiment of a method performed by a prescreen offer source in order to provide prescreened offers to the prescreen provider.

Continuing to a block 220, the borrower information is transmitted to one or more prescreened offer sources 190 (FIGS. 2-3). In one embodiment, the borrower information includes a full name and address of the borrower. For example, borrower information may comprise the following items, such as in fields of a database or spreadsheet file: first name, middle name, last name, street address, city, state, zip. In other embodiments, the borrower information may comprise fewer or additional information items, such as, for example, first name, last name, and zip code. In another embodiment, the borrower information also comprises a weekly, monthly, or yearly income, or income range, of the borrower. In other embodiments, the borrower information comprises additional information regarding the borrower. In one embodiment, referrer preferences identify one or more prescreened offer sources 190 that the borrower information should be sent to in order to receive prescreened offers. In another embodiment, the borrower information is sent to a default one or more prescreened offer sources 190.

Figure 4:
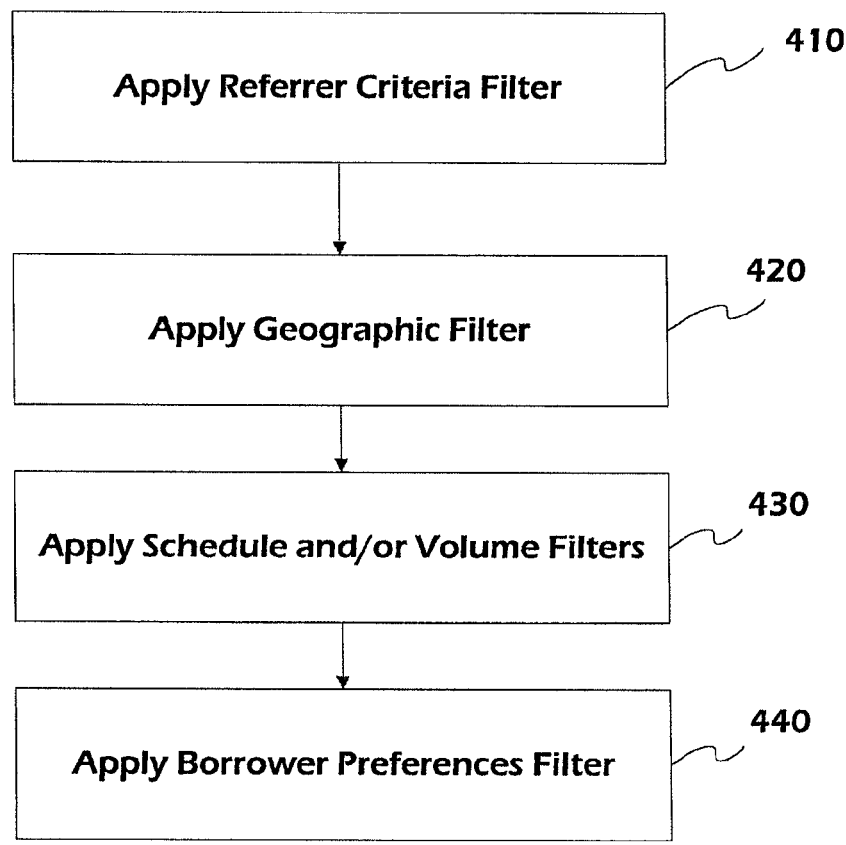
FIG. 4 is a flowchart illustrating one embodiment of a method of filtering available offers and/or filtering the prescreened offers returned from the prescreened offer source.

Next, in a block 230, the prescreen provider 100 receives the prescreened offers from the one or more prescreened offer sources 190 to which the borrower information was transmitted. The prescreened offers may be transmitted in any format available, such as in a database file, a spreadsheet file, a text file, a word processing document, an XML or HTML document, an email, or a CSV document, for example. In one embodiment, the prescreen provider 100 filters the prescreened offers received from the prescreened offer source 190 based on one or more of several possible filter sets. FIG. 4 describes several exemplary filters that may be applied by the prescreen device 100 after receiving prescreened offers from the prescreened offer source 190 and/or before transmitting the borrower information to the prescreened offer source 190.

Moving to a block 240, the prescreened offers are presented to the borrower so that the borrower may select a desired credit card offer and complete an application for the credit card offer with the credit card issuer. In one embodiment, the prescreened offers are aggregated into the prescreened offer document 166 (FIG. 1, 1A, 1B), such as one or more HTML pages, that are viewable in an Internet application running on the borrower computing device 182. In one embodiment, the presentation module 170 generates the prescreened offer document 166 based on the prescreened offers and presentation preferences of the prescreen provider and/or the referrer, which are described below with reference to the exemplary method of FIG. 5. In another embodiment, the prescreened offer document 166 comprises an email, or other electronic communication, such as a text or blackberry message, for transmission directly to the borrower computing device 182.

In an embodiment where the borrower entered information into the prescreen provider website 181 (FIG. 1A), the prescreen provider may provide the borrower with a link to the prescreened offer document 166 that may be opened in a frame of the prescreened provider website 181, or in a separate window of the borrowers browser, for example. Similarly, if the borrower information was received from a referrer, such as the third-party website 180, the prescreen device 100 may provide the referrer with a link to the prescreened offer document 166, and the link may be presented to the borrower in order to view the prescreened offers. Alternatively, the prescreen device 100 may provide the prescreened offer document 166 directly to the borrower, such as via a prescreened offer document 166 that comprises an email, for example.

In one embodiment, the prescreened offer document 166 includes prescreened offers from multiple credit card issuers. Accordingly, the prescreen device 100 and/or the prescreened offer source 190 may serve as an offer aggregator of prescreened offers by prescreening offers from multiple issuers and compiling the matched offers into a list of prescreened offers from multiple issuers. In one embodiment, the generated prescreened offer document 166 displays multiple credit card offers on a single web page. In another embodiment, the prescreened offer document 166 displays only a single offer per web page, but provides a link to subsequent offers that may be viewed by the borrower should the borrower decided not to select the first presented prescreened offer. In another embodiment, the number of offers presented to the user in a first page and subsequent pages of the prescreened offer document 166 may vary. For example, in one embodiment a first page of the prescreened offer document 166 comprises three prescreened offers, a second page comprises one prescreened offer, and a third page comprises six prescreened offers. Any other combinations of offers on various pages of a prescreened offer document 166 are also contemplated.

FIG. 3 is a flowchart illustrating one embodiment of a method performed by the prescreen offer source 190 (FIG. 1A) in order to provide prescreened offers to the prescreen device 100. As noted above, in certain embodiments multiple prescreened offer sources 190, such as the multiple sources illustrates in FIG. 1B, may be in communication with the prescreen device 100. In these embodiments, each of the prescreened offer sources 190 may perform a method similar to the exemplary method illustrated in FIG. 3. Additionally, certain of the methods described below with reference to FIG. 3 may be performed by the prescreen device 100, rather than the prescreened offer source 190. Depending on the embodiment, certain of the blocks described below may be removed, others may be added, and the sequence of the blocks may be altered.

Beginning in a block 310, eligibility requirements for a plurality of credit cards are received and stored in the offer criteria data store 168 (FIG. 1, 1A). In one embodiment, credit card issuers provide certain requirements, such as credit related criteria, biographic criteria, and/or demographic criteria, for each credit card offered by the issuer. In one embodiment, the prescreened offer source 190 comprises the offer criteria data store 168, such as in the embodiment of FIG. 1A. In another embodiment, the prescreen provider comprises the offer criteria data store 168 or a partial or full copy of the offer criteria data store 168 that is maintained by the prescreened offer source 190.

Moving to a block 320, credit data associated with the borrower is retrieved or otherwise accessed. For example, the prescreened offer source 190 may access credit data related to the borrower that is stored in the borrower credit data source 162. For example, in response to receiving a prescreening request from the prescreen device 100, the prescreened offer source 190 may request a credit report, and/or other credit related information related to the borrower, from the borrower credit data source 162. In one embodiment, other data related to the borrower, such as biographic or demographic data may be retrieved or accessed by the prescreened offer source 190.

Continuing to a block 330, a starting set of credit card offers available to the borrower is determined. In one embodiment, the number of credit card offers in the available offer data store 164 is very large, such as 1000, 2000, 10000, or more credit card offers. The third party referrer, however, may want to limit the number of credit card offers that are processed in determining matches for their referred borrowers. For example, certain referrers may have preferred credit card issuers or may want only credit cards with certain terms or incentives offered to their customers. Thus, in block 330, the referrer, such as the third-party website 180, may specify a subset of all available credit card offers that the referrer wishes to present to borrower. In one embodiment, each referrer that requests prescreening by the prescreen device 100 may select a unique starting set of credit card offers. In one embodiment, the starting sets for each referrer and/or for the prescreen provider, are stored in the available offer data store 164. In one embodiment, the starting set of credit card offers comprises all available credit card offers.

Moving to a block 340, the borrower is matched to one or more credit card offers in the determined starting set. More particularly, the credit data of the borrower, and optionally any other data related to the borrower, is compared to the respective issuer and/or credit card criteria for each offer in the starting set in order to determine which of the credit card offers the issuer would likely issue to the borrower, should the borrower complete a full application with the issuer. In one embodiment, the matching process of block 340 is performed by the prescreened offer source 190, such as a credit bureau. In this embodiment, the prescreened offer source 190 returns a list of prescreened offers to the prescreen device 100. In another embodiment, the matching process of block 340 is performed by the prescreen device 100, such as by the prescreen module 130, using the credit data from the borrower credit data source 162.

FIG. 4 is a flowchart illustrating one embodiment of a method of filtering available offers and/or filtering the prescreened offers returned from the prescreened offer source 190. As noted above, in one embodiment the prescreen provider 100 filters the available credit offers for a borrower prior to requesting prescreened offers from the prescreened offer source 190. Thus, the prescreen device 100 may provide information to the prescreened offer source 190 that narrows or broadens the starting set of credit card offers for the borrower (see block 220 of FIG. 3, for example). Any one or more of the filters described with reference to FIG. 4 may be performed prior to transmitting borrower information to the prescreened offer source 190. In another embodiment, the exemplary filters illustrated in FIG. 4 may be performed to the prescreened offers returned from the prescreened offer source 190 rather than, or in addition to, applying the filters prior to requesting prescreened offers from the prescreened offer source 190. For ease of description, each of the filters illustrated in FIG. 4 will be described as being applied to the prescreened offers received by the prescreened offer source 190. However, as noted above, any reference to application of a filter to prescreened offers should be interpreted to cover embodiments where the filter is applied to one or more available offers, such as the offers that are stored in the available offer data store. The filtering methods of FIG. 4 may be performed by the prescreened offer source and/or the prescreen device 100. Depending on the embodiment, certain of the blocks described below may be removed, others may be added, and the sequence of the blocks may be altered.

Beginning in a block 410, a filter comprising referrer criteria may be applied to the prescreened offers in order to filter the prescreened offers. These referrer criteria may be transmitted from the referrer to the prescreen device 100 and then stored there for application to borrower information for each prescreening request received from the particular referrer. In another embodiment, the referrer criteria may be transmitted from the referrer along with the borrower information. In this embodiment, the referrer criteria received with the borrower information may be used on the particular borrower. In one embodiment, the referrer criteria that is received with the borrower information may indicate that the received referrer criteria are to be used to filter prescreened offers for some, or all, subsequent borrowers for which prescreening is requested by the referrer. In one embodiment, if the referrer has previously transmitted referrer criteria to the prescreen device 100, the referrer criteria transmitted with the borrower information may supersede the previously transmitted referrer criteria, or may be applied in addition to the previously transmitted referrer criteria.

Thus, each referrer may establish unique criteria that may be used to filter the prescreened offers that are returned to the referrer and/or directly to the borrower. In one embodiment, the referrer criteria comprises limitations on the issuers for which offers should be provided, such as a list of issuers that all prescreened offers should be associated. In one embodiment, the referrer criteria comprises limitations on the interest rates, grace periods, rewards, or any other parameter of credit card offers. Thus, a particular borrower may receive different prescreened offers when the borrower information is submitted to the prescreen device 100 from two different referrers, each with different referrer criteria.

Moving to a block 420, a geographic filter may be applied to the prescreened offers. For example, in one embodiment certain credit card offers may only be available to borrowers residing in particular geographic regions. Accordingly, those credit cards that have geographic limitations may be filtered from the prescreened offers for those borrowers that do not meet the geographic limitations.

Next, in a block 430, filters based on scheduling and/or volume limits associated with certain issuers and/or specific credit cards, are applied to the prescreened offers. For example, an issuer may have daily, weekly, monthly, or yearly, limits on the number of times that the prescreen provider can present credit card offers from the issuer. Likewise, an issuer may have daily, weekly, monthly, or yearly, limits on the number of offers that will be approved by the issuer. For example, if a particular credit card has a 100 cards per month issuance limit, after 100 cards are issued in a particular month, further prescreened offers for the particular credit card may be filtered from the prescreened offers. The limits may be for all credit cards from a particular issuer, individual credit cards, or families of related credit cards. In one embodiment, if more than the limited amount of offers from a particular issuer are presented to borrowers, the prescreen provider and/or the third party referrer will not receive the bounty associated with the credit card offers. In one embodiment, an issuer may only want offers to be presented to borrowers for the issuers credit cards during a particular time of the day, such as prior to 12 PM each day or after 5 PM. Thus, the scheduling filter may also include time periods in which prescreened offers from a particular issuer, or for a particular one or more credit cards, should not be presented to potential borrowers.

Continuing to a block 440, one or more borrower preferences may be applied to the prescreened offers in order to narrower the prescreened offers to include only those that are desired by the borrower. For example, in one embodiment the borrower provides information to the prescreen provider 100 indicating one or more credit card issuer, one or more issuing banks, and/or one or more card rewards or benefits that are desirable to the borrower. Thus, the prescreen device 100 may apply the borrower preferences filter in order to filter out those prescreened offers that are not from an indicated credit card issuer, for example.

Figure 5:
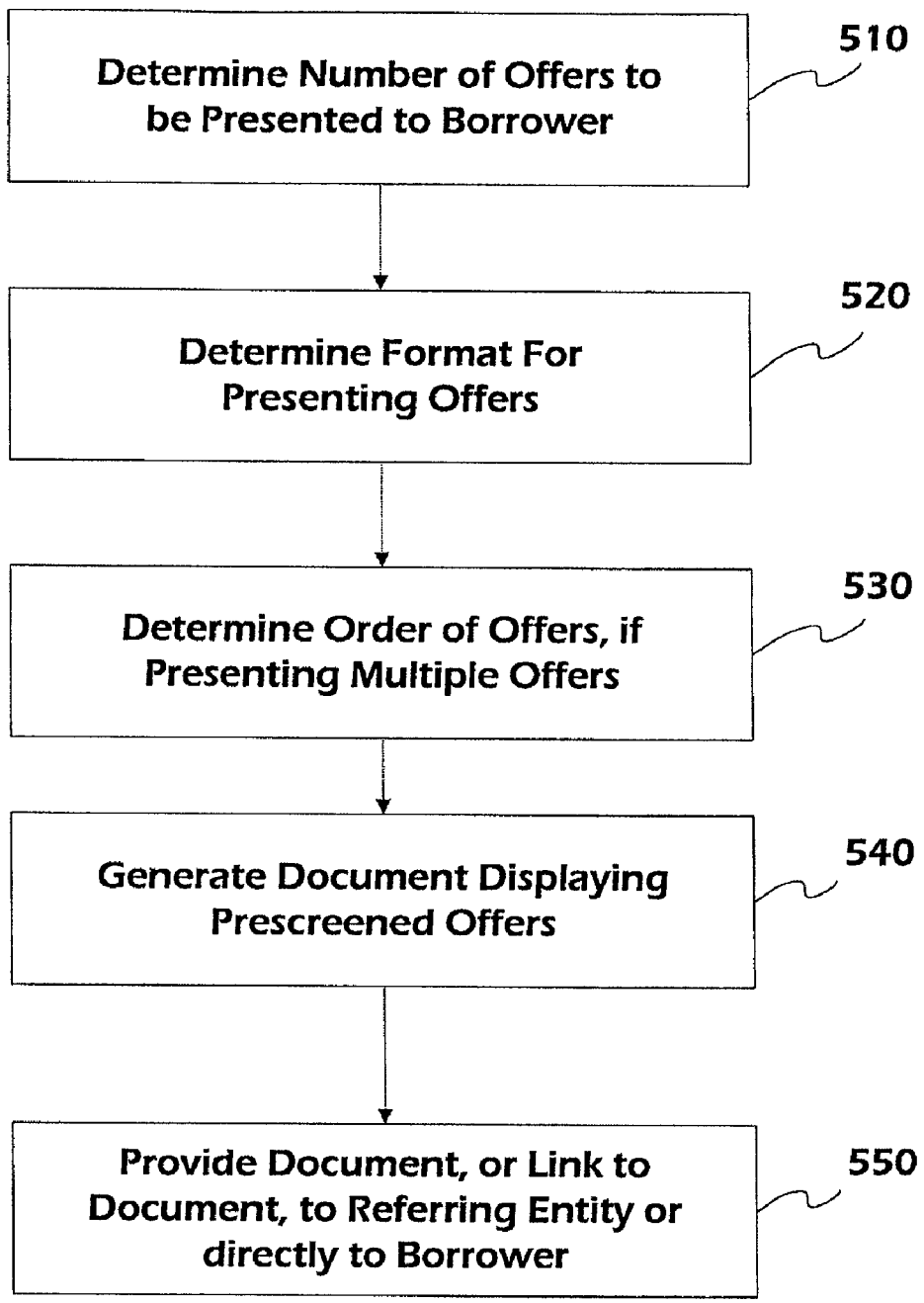
FIG. 5 is a flowchart illustrating one embodiment of a method of organizing the prescreened offers and generating a prescreened offer document, which may be presented to the borrower.

FIG. 5 is a flowchart illustrating one embodiment of a method of organizing prescreened offers and providing an indication of the offers to the referrer and/or directly to the borrower. In one embodiment, the method of FIG. 5 is performed by the presentation module 170 (FIG. 1, 1A, 1B). Depending on the embodiment, certain of the blocks described below may be removed, others may be added, and the sequence of the blocks may be altered.

Beginning in a block 510, the number of prescreened offers, where the prescreened offers may have been filtered as described above with reference to FIG. 4, that are to be presented to the borrower is determined. In one embodiment, the referrer determines a default number of prescreened offers to be presented to borrowers that are referred by the referrer. For example, one referrer may only want to display a single prescreened offer to each borrower, while another borrower may want to display 3, 5, or all of the prescreened offers to each borrower, for example. In one embodiment, the third party referrer pays a fee to the prescreen provider for each prescreened offer that is presented to a borrower by the referrer.

Continuing to a block 520, a format for presenting the prescreened offers to the borrower is determined. In one embodiment, a default format, such as in an HTML document, may be used. However, a referrer and/or borrower may request that the prescreened offers are provided in any available format, such as in an e-mail or a printed document that may be sent through the mail, for example. Thus, in one embodiment the presentation module may communicate an email comprising an indication of one or more prescreened offers directly to the borrower and/or to the referrer.

Moving to a block 530, an order of presenting multiple offers to the borrower is determined, in the case where the issuer and/or borrower want to receive multiple prescreened offers and the prescreen device has determined that multiple prescreened offers returned from the prescreened offer source 190 match the borrower. In one embodiment, the prescreened credit card offers are ranked, where the rankings determine an order in which the offers are displayed to the borrower. In one embodiment, the rankings are based only on the bounty associated with each of the prescreened offers, wherein the highest bounty offer is ranked first, while the lowest bounty of prescreened offer is ranked last. In this way, the borrower is more likely to apply for a prescreened offer that has a higher bounty. In other embodiments, the rankings may be based on a variety of other factors, which may be weighted in different combinations. Other attributes that may be considered in ranking the prescreened offers include, for example, historical click-through-rate for that offer, historical conversion rate for that offer, geographic location of the borrower, modeled overall click propensity for the borrower, which may be based on demographic analysis and historical data related to the borrower, the time of day and day of week that the prescreening is requested, and promised or desired display rates for the offer. Provisional Patent Application No. 60/824,252, titled "Systems and Methods of Ranking a Plurality of Credit Card Offers," filed on Aug. 31, 2006, which is incorporated by reference in its entirety, describes other exemplary methods of ranking prescreened offers in order.

Next, in a block 540, a prescreened offer document 166 (FIG. 1, 1A, 1b) is generated comprising information regarding the prescreened offers to be presented to the borrower. In one embodiment, the prescreened offer document 166 comprises an HTML page, such as those illustrated in FIGS. 9-11, for example. In other embodiments, the prescreened offer document 166 comprises a database or spreadsheet readable file that may be sent to the referrer and/or the borrower. In one embodiment, the referrer accesses the database or spreadsheet readable file and generates a browser viewable document, such as an HTML document, including some or all of the information regarding the prescreened offers that is included in the database or spreadsheet readable file. In one embodiment, the presentation module 170 generates an e-mail including the prescreened offers. In one embodiment, the prescreened offer document 166 is stored on a server or other Internet storage device that is controlled by the prescreen provider. Alternatively, the prescreened offer document 166 generated for a particular referrer may be stored on a server or Internet storage device controlled by the particular referrer.

Continuing to a block 550, the generated prescreened offer document 166 or a link to the document is provided to the referrer and/or the borrower. In an embodiment where the borrower information is received directly from the borrower, such as via the prescreen provider website 181 (FIG. 1A), the prescreened offer document 166 or link to the document may be sent directly to the borrower. For example, if the borrower has entered information into the prescreen provider website 181, the generated prescreened offer document 166 may be displayed to the borrower in response to the borrower selecting a link that submits the borrower information for pre-screening. More particularly, because the prescreening processes described herein advantageously may operate in real-time, such as about 1-10 seconds from the time the borrower information is received by the prescreen device 100 until the prescreened offer document 166 is ready from presentation, the prescreen provider website 181 may link to the generated prescreened offer document 166 in response to the borrower selecting a link that submits borrower information to the prescreen device 100 for prescreening. Thus, in this embodiment, the borrower is not required to enter any further information or select any further links in order to be presented with prescreened credit card offers. In other embodiments, the prescreened offer document 166 comprises an email that is sent to the borrower and/or referrer or a printed document that is mailed to the borrower and/or referrer, for example.

In an embodiment where the borrower information is received from a third party referrer, the referrer may indicate how the prescreened offer document 166 is to be delivered to the referrer and/or the borrower. For example, a link to the prescreened offer document 166 may be transmitted to the referrer as soon as it is available so that the referrer may display the document to the borrower. In one embodiment, the borrower may display the prescreened offer document 166 in a frame of the referrer's website, such as third party website 180. In another embodiment, the referrer may request that the prescreen device 100 deliver the document to the borrower and/or the referrer via email. In this embodiment, the borrower may receive an email with the prescreened offers, either in the email body or in an attachment to the email, for example, within seconds after authorizing the referrer to provide prescreened offers. In one embodiment, the referrer may submit borrower information to the prescreen device 100 from one or more customers of the referrer without the customers requesting that prescreened offers are provided. The presentation module 170 may transmit the prescreened offer documents 166 to the respective customers of the referrer in emails, or may provide a link to the prescreened offer documents that the referrer may present to the respective borrowers when they next log into the referrer website. The prescreened offer documents 166 may be transmitted and/or accessed by the prescreen provider website 181, referrer, and/or borrower in any other manner know in the art, or later developed.

Figure 6:
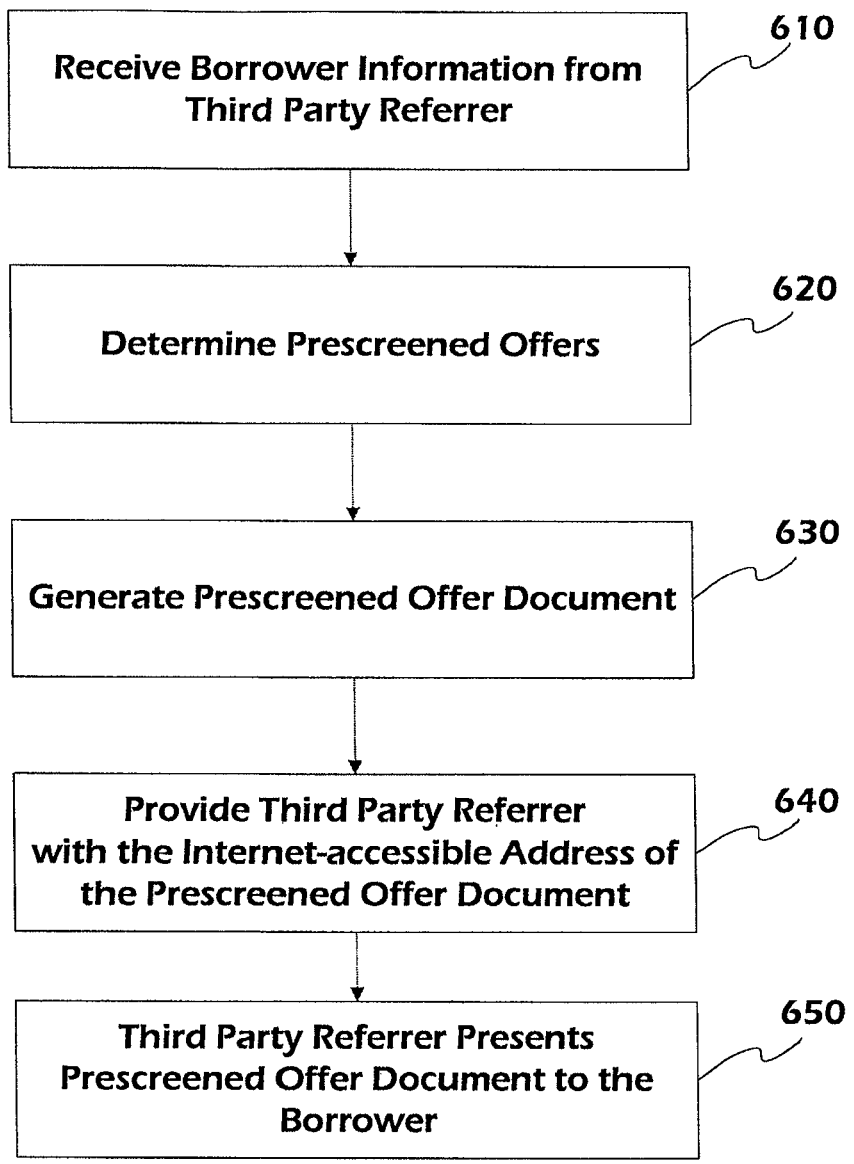
FIG. 6 is a flowchart illustrating one embodiment of a method of interfacing with a third party referrer in order to provide prescreened credit card offers.

FIG. 6 is a flowchart illustrating one embodiment of a method of interfacing with a third party referrer in order to provide prescreened credit card offers. In one embodiment, the prescreen device 100 provides prescreened offers to borrowers via a prescreened offer document 166 that may be viewed in a frame or window of the third party referrer website 180, for example. Advantageously, in one embodiment the referrer is not required to generate the prescreened offer document 166, such as one or more HTML pages, but instead the referrer may simply link to the URL of the generated prescreened offer document 166 in order to present prescreened offers to visitors of the referrer website. Depending on the embodiment, certain of the blocks described below may be removed, others may be added, and the sequence of the blocks may be altered.

Beginning in a block 610, borrower information is received from the third party referrer. In one embodiment, the borrower information is received in an XML document, for example. In other embodiments, the borrower information may be transmitted to the prescreen device 100 in any other format. In one embodiment, borrower information for multiple borrowers is combined into a single batch file that is transmitted to the prescreen device 100, such as via email or FTP, for example.

Continuing to a block 620, prescreened offers for the borrower are determined. For example, a prescreening process, such as the process described with reference to FIG. 3 may be performed. Additionally, a filtering of prescreened offers, such as by using the filtering methods described with reference to FIG. 4, may be performed on the prescreened offers and/or to the available offers.

Moving to a block 630, a prescreened offer document 166 (FIG. 1, 1A, 1B), such as a browser viewable document, is generated including information regarding the prescreened offers. For example, in one embodiment the presentation module 170 determines which of the prescreened offers should be included in the prescreened offer document 166 and/or an order of the offers. FIG. 5 illustrates an exemplary method that may be performed in generating the prescreened offer document 166, such as an HTML document, that may be presented to the borrower.

Next, in a block 640, the third party referrer is provided with the prescreened offer document 166 and/or a link to the prescreened offer document 166. In one embodiment, an HTML prescreened offer document is stored on a server that is accessible to the referrer and borrower. In this embodiment, the prescreen device 100 transmits the link to the HTML prescreened offer document after it is generated by the presentation module 170, or possibly even before generation of the document is complete. In one embodiment, the presentation module 170 may have a predetermined naming syntax for prescreened offer documents 166 from a particular referrer. For example, the prescreened offer documents may be named offers-[borrower last name]-[borrower first name].html and stored in a predetermined location on a server such that as soon as the borrower information is submitted to the prescreen device 100, the referrer knows where to access the prescreened offer document. In another embodiment, the referrer may request the prescreened offer document 166, or the location of the prescreened offer document 166, at any time after transmitting the borrower information to the prescreen device 100. In this embodiment, if the prescreened offer document 166 is not yet available when requested by the referrer, the prescreen device 100 may indicate that the document is not yet available and the referrer may send one or more subsequent requests to the prescreen device 100 until the location of the document is returned.

Continuing to a block 650, the referrer presents the generated prescreened offer document 166 to the borrower, such as in a frame or window of the referrer website. As noted above, because the prescreening processes described herein may advantageously operate in real-time, such as about 1-10 seconds from the time borrower information is received by the prescreen device 100 until the prescreened offer document 166 is ready from presentation, the referrer may present the prescreened offer document to the borrower in response to the borrower selecting a link requesting prescreened offers. In other embodiments, the referrer may request prescreened offers for customers without the customers first requesting the prescreened offers. In this embodiment, the referrer may present the prescreened offers to the borrower when the borrower logs into the referrer website, for example. In either case, the referrer can provide prescreened offers to their customers, or other visitor's of their website, with minimal effort, where the acceptance of a customer for a credit card could increase purchases by the customer at the referrer's website.

Figure 7:
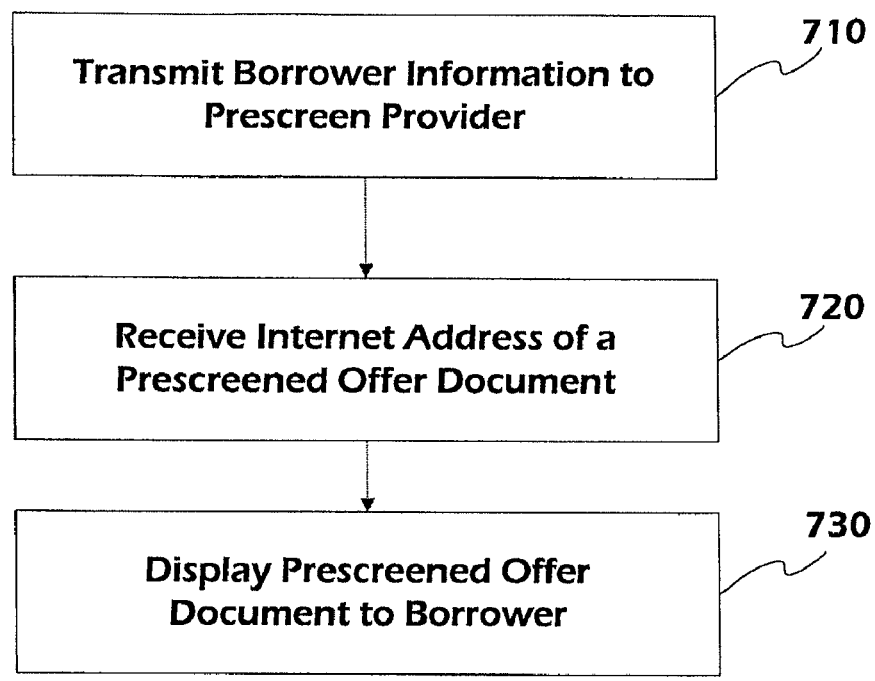
FIG. 7 is a flowchart illustrating one embodiment of a method of interfacing with the prescreen provider in order to provide prescreened credit card offers.

FIG. 7 is a flowchart illustrating one embodiment of a method for a referrer to interface with the prescreen device 100 in order to provide prescreened credit card offers to users of the referrers website, for example. In one embodiment, third-party websites may provide prescreened credit card offers to their customers by simply providing customer information to the prescreen device 100 and then directing the customer to the generated customer-specific prescreened offer document 166 provided by the prescreen device 100. In one embodiment, the third-party need only send a customer name and address in order to initiate the prescreen process. Depending on the embodiment, certain of the blocks described below may be removed, others may be added, and the sequence of the blocks may be altered.

Beginning in a block 710, information regarding the potential borrower is transmitted to the prescreen device 100, such as via the network 160. As described above, the borrower information may be in any format and may be transmitted to the prescreen device 100 in any available manner. In one embodiment, the borrower information is stored in an XML or CSV document and transmitted to the prescreen provider 100. The borrower information may comprise a full name of the borrower in addition to portions or all of an address of the borrower. For example, in one embodiment, the full name and zip code of the borrower provides sufficient information to the prescreen provider to match the borrower to one or more credit card offers. In other embodiments, the full name and the full address of the borrower is needed. In other embodiments, the surname of the borrower in addition to certain address information may be sufficient.

Continuing to a block 720, the address of the prescreened offer document 166 is received by the referrer. In one embodiment, the URL to a HTML prescreened offer document is transmitted to the referrer as soon as the document is stored on an Internet-accessible server. In another embodiment, the URL may be transmitted to the referrer in response to a request for the URL from the referrer. In other embodiments, a copy of the prescreened offer document 166 may be transmitted to the referrer. In some embodiments, the prescreened offer document 166 may comprise multiple pages, such as multiple linked HTML documents.

Next, in a block 730, the generated HTML prescreened offer document is displayed to the borrower, such as in a frame of the referrer's website. Alternatively, the prescreened offer document may be displayed in a separate window of a web browser or custom software application, such as a third party specific software, running on the borrower computing device 182. In one embodiment, a link to the respective credit card issuer, or to an agent of the issuer, is associated with each of the credit card offers displayed to the borrower. In one embodiment, the HTML document, or a link to the HTML prescreened offer document, may be transmitted to the referrer.

FIG. 8 is one embodiment of a screenshot of a user interface that allows a potential borrower to enter information for submission to a prescreen provider. In one embodiment, the user interface illustrated in FIGS. 8-14 is part of the prescreen provider website 181 (FIG. 1A). Thus, in these embodiments, the borrower information is entered directly into a user interface operated by the prescreen provider. In other embodiments, third party referrers may present user interfaces similar to those illustrated in FIGS. 8-14.

In the embodiment of FIG. 8, the user interface comprises a quick match form 810, a browse area 820, and a slow prescreen area 830. In this embodiment, prescreened offers for the borrower may be most quickly received by entering borrower information into the fields of the quick match form 810. In the embodiment of FIG. 8, the quick match form 810 includes first name, last name, home address, cite, state, and zip code fields. In one embodiment, the borrower must provide valid information in each of these fields before the prescreening process will begin. In other embodiments, however, not all of the fields need to be filled and/or the quick match form 810 may comprise additional fields. In another embodiment, the prescreened offer source 190 and/or the credit bureau from which credit information may be accessed by the prescreened offer source 190 also require an income amount or income range of the borrower. Thus, in one embodiment the quick match form 810 also comprises a field for entry of an income range by the borrower, or for selection of an income range, such as from a drop-down menu.

After entering information into the fields of the quick match form 810, the borrower may initiate the prescreening process by selecting the link 812, which comprises a button in the embodiment of FIG. 8. As noted above, in response to selecting the link 812, the prescreen provider website may display the generated prescreen results document to the borrower, such as the HTML documents that are illustrated with reference to FIGS. 9-11, for example. In one embodiment, the prescreen provider website 181, or third-party website 180, may comprises only fields for the borrower to enter the information that is necessary for prescreening, such as the fields illustrated in the quick match form 810.

The browse area 820 allows the borrower to filter the available credit card offers according to card type or issuing bank. In one embodiment, when the borrower enters information in either of these fields, such as by using drop down boxes, the user interface displays one or more invitations to apply (ITA) for credit cards matching the selected filter attributes. In this embodiment, the ITAs that are presented to the borrower are not prescreened offers, but only credit cards that match certain selected filters that the borrower has selected. The browse areas 820 also comprises a plurality of card categories 822 that may be selected by the borrower in order to view ITAs for credit cards that are within selected categories. In one embodiment, the categories of credit cards, the types of cards, and/or the issuer bank selected by the borrower are used as part of the borrower preferences filter that is discussed above with reference to FIG. 4. For example, if the borrower wishes to be prescreened for credit card offers, after browsing one or more ITAs in response to selected filters in the browse area 820, filtering of the prescreened offers may be based at least partly on the browsing activities of the borrower.

The slow prescreen area 830 allows the borrower to enter non-identifying information that may be used to filter ITAs and/or prescreened offers. In the embodiment illustrated in FIGS. 8-14, if the borrower enters information in the fields of the slow prescreen area 830 and then selects the link 832, the borrower will be presented with a second user interface that requests additional information from the user, such as the user interface displayed in FIG. 12, for example, and may present one or more ITAs to the borrower based on the information entered into the slow prescreen area 830. In the embodiment of FIG. 8, the slow prescreen area 830 includes drop-down boxes that allow the borrower to select a credit profile, one or more desired card benefits, and an occupational status. In one embodiment, the selections made by the borrower in the slow prescreen area 830 are used in the filtering that is perform on prescreened offers returned from the prescreened offer source 190, or to the available offers prior to prescreening by the prescreened offer source 190.

FIGS. 9 and 10 illustrate one embodiment of screenshots of a prescreened results document presenting credit card offers to the borrower. More particularly, the screenshot 900 (FIG. 9) illustrates a first page of an exemplary prescreened offer document and the screenshot 1000 (FIG. 10) illustrates a second page of the prescreened offer document. In one embodiment, the user interface illustrated in FIG. 9 is presented to the borrower in response to selecting link 812 (FIG. 8), after entering the requested information in the quick match form 810. Alternatively, the user interface illustrated in FIG. 9 may be presented to the borrower after the borrower views one or more pages of the user interface displaying ITAs that have been filtered by criteria entered by the borrower, such as in the browse area 820 (FIG. 8) or the slow prescreen area (832). In another embodiment, the prescreen results document, or a link to the prescreen results document, such as a link to the URL of the user interface 900, may be transmitted to a third party referrer.

Each of FIGS. 9 and 10 illustrates information regarding a prescreened credit card offer for a particular borrower. As shown in these figures, the user interfaces 900, 1000 each display a single prescreened offer. Thus, the borrower views the first prescreened offer in the user interface of FIG. 9, and then, should the borrower want to view another prescreened offer, the borrower may select a link 920 that is linked to the user interface illustrated in FIG. 10. Alternatively, if the borrower wants to apply for the prescreened offer in FIG. 9, the borrower may select a link 910 that is linked to a website hosted by the credit card issuer, or an agent of the credit card issuer, of the displayed prescreened credit card offer. Likewise, the user interface of FIG. 10 includes a link 1010 that the borrower may select to apply for the illustrated Discover card, and a link 1020 that the borrower may select to view any additional prescreened offers. Thus, the prescreened results document may comprise multiple pages, such as multiple HTML pages, where each page displays a singled prescreened offer. In one embodiment, the highest ranked prescreen offer is displayed to the borrower first, such as in the user interface of FIG. 9, followed by the second highest ranked prescreened offer in the user interface of FIG. 10, and so on. In one embodiment, if there are no prescreened offers for a borrower, a user interface comprising one or more ITAs is presented to the borrower.

FIG. 11 is one embodiment of a screenshot of a user interface 1100 for presenting multiple prescreened credit card offers to a borrower, along with respective links 1110 associated with the prescreened offers that may be selected in order to apply for the respective credit card. In the embodiment of FIG. 10, rather than display a single prescreened offer to the borrower on each page of the prescreened results document, such as is illustrated in FIGS. 9-10, for example, the user interface 1100 concurrently displays three prescreened offers. In one embodiment, fewer, such as 2, or more, such as 4, 5, 6, 7, 8, 10, or 15 credit card offers may be displayed in a single page of the prescreened results document. In one embodiment, the highest ranked prescreened offer is displayed on a left side, or top, of the prescreened results document, while the lowest ranked prescreened offer is displayed on a right side, or bottom, of the prescreened results document. In one embodiment, the user interface 1100 is generated by the presentation module 170.

FIG. 12 is one embodiment of a screenshot of a second user interface 1200 requesting additional information from the borrower. In one embodiment, the user interface 1200 is presented to the borrower in response to the borrower entering information in the slow prescreen area 810 and selecting the link 812. In other embodiments, the user interface 1200 may be presented to the borrower in response to the borrower selecting one or more browsing filters, such as those in the browse area 820. The exemplary user interface 1200 comprises information regarding ITAs 1210A, 1210B for credit cards that are within a group of cards that satisfy the filter selected by the borrower, such as in the slow prescreen area 810 and/or the browse area 810. However, because the borrower has not yet entered any personal information that may be used to perform the prescreening process, such as full name and address, the credit cards displayed in the user interface 1200 are only invitations to apply for credit cards, and not prescreened credit card offers.

In the exemplary user interface 1200, a second slow prescreen area 1220 is presented to the user, requesting additional information regarding the borrower. In this embodiment, the second slow prescreen area 1220 requests information regarding the borrowers credit card payment habits and requests that the borrower identify a financial institution where the borrower maintains a primary checking or savings account. In one embodiment, the information provided by the borrower in the second slow prescreen area 1220 is used in further narrowing a list of ITAs for the borrower that may be displayed to the borrower in response to the borrower selecting the continue link 1230, for example. In another embodiment, the information provided by the borrower in the second slow prescreen area 1220 may be used in the filtering of prescreened offers should the borrower decide to later enter borrower information that is sufficient to perform the prescreening process.

Figure 13:
FIG. 13 is one embodiment of a screenshot of a third user interface requesting additional information from the borrower.

FIG. 13 is one embodiment of a screenshot of a third user interface 1300 requesting additional information from the borrower. In one embodiment, the user interface 1300 is presented to the borrower in response to the borrower entering information in the second slow prescreen area 1210 and selecting the link 1230 (FIG. 12). In other embodiments, the user interface 1300 may be presented to the borrower in response to the borrower selecting one or more browsing filters, such as those in the browse area 820. The exemplary user interface 1300 comprises information regarding ITAs 1310A, 1310B that have been further filtered by the information provided by the borrower in the second slow prescreen area 1220. However, because the borrower has not yet entered any personal information that may be used to perform the prescreening process, such as full name and address, the credit cards displayed in the user interface 1300 are only invitations to apply for credit cards, and not prescreened credit card offers.

In the exemplary user interface 1300, a third slow prescreen area 1320 is presented to the user, requesting additional information regarding the borrower. In this embodiment, the third slow prescreen area 1320 requests information regarding the borrower that may be used to perform a prescreening process on the borrower and present the borrower with prescreened credit card offers. Thus, the slow prescreen area 1320 comprises the same fields as the quick match form 810 of FIG. 8. More particularly, the slow prescreen area 1320 requests information regarding the borrower's first name, last name, home address, city, state, and zip code. In one embodiment, in response to the borrower entering the requested information in the slow prescreen area 1320 and selecting the continue link 1330, a prescreened offer document displaying one or more prescreened offers may be presented to the borrower, such as, for example, the user interface 900 (FIG. 9) or the user interface 1100 (FIG. 11). In one embodiment, the prescreened offers that are presented to the borrower are filtered using the information that is provided in the first and second slow prescreen areas 830, 1230.

Figure 14:
FIG. 14 is one embodiment of a screenshot of a fourth user interface displaying invitations to apply for credit card offers that have been filtered according to the information provided by the borrower.

FIG. 14 is one embodiment of a screenshot of a fourth user interface 1400 displaying invitations to apply for credit card offers that have been filtered according to the information provided by the borrower, such as in one or more of the user interfaces 800, 1200, 1300. In one embodiment, the user interface 1400 is presented to the borrower if no prescreened offers are returned from the prescreening process, in response to the borrower entering the requested information in either the quick match form 820 of the third slow prescreen area 1320.

The foregoing description details certain embodiments of the invention. It will be appreciated, however, that no matter how detailed the foregoing appears in text, the invention can be practiced in many ways. The use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method of prescreening a potential borrower for each of a plurality of credit card offers, the plurality of credit card offers comprising at least a first credit card offer associated with a first lender and a second credit card offer associated with a second lender, the method comprising:

receiving at a first computing system comprising one or more computing devices borrower information associated with a borrower, wherein the borrower information is not sufficient to complete an application for a credit card and comprises a first name, a last name, and one or more of: a street address, a city, a state, and a zip code, wherein the borrower information is received via one or more networks from a third-party referrer computing system that receives the borrower information from a borrower computing system operated by the borrower;

transmitting the borrower information from the first computing system to a prescreened offer source computing system configured to access credit data related to the borrower and determine zero or more prescreened credit card offers indicating credit cards that the borrower would likely be accepted for by the respective issuer;

receiving from the prescreened offer source computing system information regarding the zero or more prescreened credit card offers;

in response to receiving one or more prescreened credit card offers, generating at the first computing system a browser-viewable prescreened offer document comprising information regarding at least one of the prescreened credit card offers, the prescreened offer document comprising a link associated with each prescreened offer, wherein the links are associated with browser-viewable documents that allow the borrower to apply for respective prescreened offers, storing the prescreened offer document at a network location accessible to the third-party referrer computing system, wherein a filename of the stored prescreened offer document is determined based on a predefined format so that the third-party referrer computing system can access the prescreened offer document without receiving the filename from the first computing system, and transmitting the prescreened offer document, a link to the prescreened offer document, or an indication that the prescreened offer document has been stored at the network location to the third-party referrer computing system for access by the borrower computing system; and in response to receiving zero prescreened credit card offers, generating at the first computing system a browser-viewable invitation to apply document comprising information regarding one or more invitations to apply for one or more respective credit cards, storing the invitation to apply document at a network location accessible to the third-party referrer computing system, wherein a filename of the invitation to apply document is determined based on a predefined format so that the third-party referrer can access the invitation to apply document without receiving the filename from the first computing system, and transmitting the invitation to apply document, a link to the invitation to apply document, or an indication that the prescreened offer document has been stored at the network location to the third-party referrer computing system for access by the borrower computing system.

2. The method of claim 1, wherein the prescreened offer document comprises multiple pages that are separately viewable in a browser.

3. The method of claim 1, wherein the prescreened offer source computing system is configured to:

access data associated with the borrower;

access acceptance criteria for each of a plurality of available credit cards offered by at least two different credit card issuers; and compare the data to the acceptance criteria for each of the plurality of available credit cards in order to determine zero or more credit cards that would likely be issued to the borrower.

4. The method of claim 1, wherein the prescreened credit card offers comprise firm offers of credit.

5. The method of claim 1, wherein the borrower does not provide authorization to transmit the borrower information to the first computing system.

6. The method of claim 1, wherein the borrower is not aware that the prescreening method is being performed until the browser-viewable prescreened offer document is presented to the borrower by the borrower computing system.

7. The method of claim 1, wherein an entity associated with the third-party referrer computing system receives a monetary payment in response to the borrower's establishment of a credit card account for one of the prescreened credit card offers as a result of the borrower accepting an offer via the prescreened offer document.

8. The method of claim 1, wherein the third-party referrer computing system receives the borrower information from the borrower via one or more browser-viewable documents comprising information entry fields for entry of borrower information by a borrower computing system under direction of the borrower.

9. A computing system comprising:

a processor;

a computer readable medium storing machine-executable instructions including one or more modules configured for execution by the processor in order to cause the computing system to:

receive borrower information associated with a borrower, wherein the borrower information comprises a first name, a last name, and one or more of: a street address, a city, a state, and a zip code, wherein the borrower information is received via one or more networks from a third-party referrer computing system that receives the borrower information from a borrower computing system;

transmit the borrower information from the computing system to a prescreened offer source computing system configured to access credit data related to the borrower and determine zero or more prescreened credit card offers indicating credit cards that the borrower would likely be accepted for by the respective issuer;

receive from the prescreened offer source computing system information regarding the zero or more prescreened credit card offers;

respond to receiving one or more prescreened credit card offers by:

generating a browser-viewable prescreened offer document comprising information regarding at least one of the prescreened credit card offers;

storing the prescreened offer document at a network location accessible to the third-party referrer computing system, wherein a filename of the stored prescreened offer document is determined based on a predefined format so that the third-party referrer computing system can access the prescreened offer document without receiving the filename from the computing system, and transmitting the prescreened offer document, a link to the prescreened offer document, or an indication that the prescreened offer document has been stored at the network location to the third-party referrer computing system for access by the borrower computing system; and respond to receiving zero prescreened credit card offers by:

generating a browser-viewable invitation to apply document comprising information regarding one or more invitations to apply for one or more respective credit cards, storing the invitation to apply document at a network location accessible to the third-party referrer computing system, wherein a filename of the invitation to apply document is determined based on a predefined format so that the third-party referrer can access the invitation to apply document without receiving the filename from the computing system, and transmitting the invitation to apply document, a link to the invitation to apply document, or an indication that the prescreened offer document has been stored at the network location to the third-party referrer computing system for access by the borrower computing system.

10. The computing system of claim 9, wherein the prescreened offer document comprises multiple pages that are separately viewable in a browser.

11. The computing system of claim 9, wherein the prescreened credit card offers comprise firm offers of credit.

12. The computing system of claim 9, wherein the borrower does not provide authorization to transmit the borrower information to the computing system.

13. The computing system of claim 9, wherein the borrower is not aware that the prescreening method is being performed until the browser-viewable prescreened offer document is presented to the borrower.

14. The computing system of claim 9, wherein an entity associated with the third-party referrer computing system receives a monetary payment in response to the borrower's establishment of a credit card account for one of the prescreened credit card offers as a result of the borrower accepting an offer via the prescreened offer document.

15. A non-transitory tangible computer readable medium having instructions stored thereon, the instructions configured for reading by a first computing system in order to cause the first computing system to perform operations comprising:

receiving at a first computing system comprising one or more computing devices borrower information associated with a borrower, wherein the borrower information comprises a first name, a last name, and one or more of: a street address, a city, a state, and a zip code, wherein the borrower information is received via one or more networks from a third-party referrer computing system that receives the borrower information from a borrower computing system operated by the borrower;

transmitting the borrower information from the first computing system to a prescreened offer source computing system configured to access credit data related to the borrower and determine zero or more prescreened credit card offers indicating credit cards that the borrower would likely be accepted for by the respective issuer;

receiving from the prescreened offer source computing system information regarding the zero or more prescreened credit card offers;

in response to receiving information indicating one or more prescreened credit card offers for the borrower,
- generating at the first computing system a browser-viewable prescreened offer document comprising information regarding at least one of the prescreened credit card offers,
- storing the prescreened offer document at a network location accessible to the third-party referrer computing system; and
- transmitting an indication that the prescreened offer document has been stored at the network location to the third-party referrer computing system for access by the borrower computing system; and in response to receiving zero prescreened credit card offers,
- generating at the first computing system a browser-viewable invitation to apply document comprising information regarding one or more invitations to apply for one or more respective credit cards,
- storing the invitation to apply document at a network location accessible to the third-party referrer computing system; and
- transmitting an indication that the prescreened offer document has been stored at the network location to the third-party referrer computing system for access by the borrower computing system.

16. The non-transitory tangible computer readable medium of claim 15, wherein the prescreened offer document comprises multiple pages that are separately viewable in a browser.

17. The non-transitory tangible computer readable medium of claim 15, wherein the prescreened credit card offers comprise firm offers of credit.

18. The non-transitory tangible computer readable medium of claim 15, wherein the borrower does not provide authorization to transmit the borrower information to the first computing system.

19. The non-transitory tangible computer readable medium of claim 15, wherein the borrower is not aware that the prescreening method is being performed until the browser-viewable prescreened offer document is presented to the borrower.

20. The non-transitory tangible computer readable medium of claim 15, wherein an entity associated with the third-party referrer computing system receives a monetary payment in response to the borrower's establishment of a credit card account for one of the prescreened credit card offers as a result of the borrower accepting an offer via the prescreened offer document.

* * * * *